(12) United States Patent
Al-Ali et al.

(10) Patent No.: US 9,775,545 B2
(45) Date of Patent: Oct. 3, 2017

(54) MAGNETIC ELECTRICAL CONNECTOR FOR PATIENT MONITORS

(75) Inventors: Ammar Al-Ali, San Juan Capistrano, CA (US); Eric Karl Kinast, Santa Ana, CA (US)

(73) Assignee: Masimo Corporation, Irvine, CA (US)

( * ) Notice: Subject to any disclaimer, the term of this patent is extended or adjusted under 35 U.S.C. 154(b) by 347 days.

(21) Appl. No.: 13/246,768

(22) Filed: Sep. 27, 2011

(65) Prior Publication Data

US 2012/0088984 A1    Apr. 12, 2012

Related U.S. Application Data

(60) Provisional application No. 61/387,426, filed on Sep. 28, 2010.

(51) Int. Cl.
*A61B 5/00* (2006.01)
*A61B 5/1455* (2006.01)
*A61B 5/0476* (2006.01)

(52) U.S. Cl.
CPC ........ *A61B 5/14551* (2013.01); *A61B 5/0476* (2013.01); *A61B 5/14553* (2013.01); *A61B 5/6814* (2013.01); *A61B 2562/227* (2013.01); *A61B 2562/245* (2013.01)

(58) Field of Classification Search
CPC . A61B 5/0476; A61B 5/0006; A61B 5/04004; A61B 5/0478; A61B 5/14552; A61B 5/6814; A61B 2562/164; A61B 5/04282; A61B 18/1233; A61B 2018/00083; G08C 17/06
USPC .................................................. 600/300–301
See application file for complete search history.

(56) References Cited

U.S. PATENT DOCUMENTS

| | | | |
|---|---|---|---|
| 3,811,094 A * | 5/1974 | Lee | 330/59 |
| 4,223,680 A | 9/1980 | Jobsis | |
| 4,281,645 A | 8/1981 | Jobsis | |
| 4,321,930 A | 3/1982 | Jobsis et al. | |
| 4,380,240 A | 4/1983 | Jobsis et al. | |
| 4,510,938 A | 4/1985 | Jobsis et al. | |
| 4,796,184 A | 1/1989 | Bahr et al. | |
| 4,803,997 A | 2/1989 | Bowman | |
| 4,805,623 A | 2/1989 | Jobsis | |
| 4,848,345 A * | 7/1989 | Zenkich | 607/2 |
| 4,901,238 A | 2/1990 | Suzuki et al. | |

(Continued)

FOREIGN PATENT DOCUMENTS

EP      505491          9/1992
EP      0 541 393       11/1992

(Continued)

OTHER PUBLICATIONS

US 8,845,543, 09/2014, Diab et al. (withdrawn)

(Continued)

*Primary Examiner* — Adam J Eiseman
*Assistant Examiner* — Shirley Jian
(74) *Attorney, Agent, or Firm* — Knobbe Martens Olson & Bear, LLP

(57) ABSTRACT

The present disclosure relates to an electrical connector for providing signal isolation between various components of a physiological monitoring system. In an embodiment, the electrical connector is placed between a sensor and associated monitoring system and includes a physical barrier and inductive components.

5 Claims, 14 Drawing Sheets

(56) References Cited

U.S. PATENT DOCUMENTS

| | | | |
|---|---|---|---|
| 4,907,876 | A | 3/1990 | Suzuki et al. |
| 4,908,762 | A | 3/1990 | Suzuki et al. |
| 4,917,116 | A | 4/1990 | LaViola et al. |
| 4,928,696 | A | 5/1990 | Henderson et al. |
| 4,938,218 | A | 7/1990 | Goodman et al. |
| 4,957,000 | A | 9/1990 | Delpy et al. |
| 4,960,128 | A | 10/1990 | Gordon et al. |
| 4,964,408 | A | 10/1990 | Hink et al. |
| 4,967,038 | A | 10/1990 | Gevins et al. |
| 4,972,331 | A | 11/1990 | Chance |
| 4,996,992 | A | 3/1991 | LaViola et al. |
| 5,022,403 | A | 6/1991 | LaViola |
| 5,032,024 | A | 7/1991 | Cope |
| 5,038,782 | A | 8/1991 | Gevins et al. |
| 5,041,187 | A | 8/1991 | Hink et al. |
| 5,069,213 | A | 12/1991 | Polczynski |
| 5,090,415 | A | 2/1992 | Yamashita et al. |
| 5,099,842 | A | 3/1992 | Mannheimer et al. |
| 5,101,830 | A | 4/1992 | Duffy et al. |
| 5,103,829 | A | 4/1992 | Suzuki et al. |
| 5,109,849 | A | 5/1992 | Goodman et al. |
| 5,119,815 | A | 6/1992 | Chance |
| 5,122,974 | A | 6/1992 | Chance |
| 5,154,180 | A | 10/1992 | Blanchet et al. |
| 5,163,438 | A | 11/1992 | Gordon et al. |
| 5,179,570 | A | 1/1993 | Imran |
| 5,179,957 | A | 1/1993 | Williams |
| 5,181,520 | A | 1/1993 | Wertheim et al. |
| 5,187,672 | A | 2/1993 | Chance et al. |
| 5,195,531 | A | 3/1993 | Bennett |
| 5,211,174 | A | 5/1993 | Imran |
| 5,213,105 | A | 5/1993 | Gratton et al. |
| 5,218,962 | A | 6/1993 | Mannheimer et al. |
| 5,220,502 | A | 6/1993 | Qian et al. |
| 5,226,417 | A | 7/1993 | Swedlow et al. |
| 5,228,440 | A | 7/1993 | Chung et al. |
| 5,247,932 | A | 9/1993 | Chung et al. |
| 5,253,646 | A | 10/1993 | Delpy et al. |
| 5,280,793 | A | 1/1994 | Rosenfeld |
| 5,289,822 | A | 3/1994 | Highe et al. |
| 5,295,482 | A | 3/1994 | Clare et al. |
| 5,299,118 | A | 3/1994 | Martens et al. |
| 5,299,822 | A | 4/1994 | Mayr et al. |
| 5,307,818 | A * | 5/1994 | Segalowitz .............. 600/509 |
| 5,319,355 | A | 6/1994 | Russek |
| 5,327,888 | A | 7/1994 | Imran |
| 5,331,959 | A | 7/1994 | Imran |
| 5,337,744 | A | 8/1994 | Branigan |
| 5,337,745 | A | 8/1994 | Benaron |
| 5,341,805 | A | 8/1994 | Stavridi et al. |
| 5,345,934 | A | 9/1994 | Highe et al. |
| 5,353,799 | A | 10/1994 | Chance |
| 5,361,773 | A | 11/1994 | Ives |
| D353,195 | S | 12/1994 | Savage et al. |
| D353,196 | S | 12/1994 | Savage et al. |
| 5,377,674 | A | 1/1995 | Kuestner |
| 5,377,675 | A | 1/1995 | Ruskewicz et al. |
| 5,377,676 | A | 1/1995 | Vari et al. |
| 5,386,827 | A | 2/1995 | Chance et al. |
| 5,402,778 | A | 4/1995 | Chance |
| 5,406,957 | A | 4/1995 | Tansey |
| 5,413,098 | A | 5/1995 | Benaron |
| D359,546 | S | 6/1995 | Savage et al. |
| 5,421,329 | A | 6/1995 | Casciani et al. |
| 5,424,843 | A | 6/1995 | Tromberg et al. |
| 5,431,170 | A | 7/1995 | Mathews |
| D361,840 | S | 8/1995 | Savage et al. |
| 5,441,054 | A | 8/1995 | Tsuchiya |
| D362,063 | S | 9/1995 | Savage et al. |
| 5,450,855 | A | 9/1995 | Rosenfeld et al. |
| 5,452,717 | A | 9/1995 | Branigan et al. |
| 5,452,718 | A | 9/1995 | Clare et al. |
| D363,120 | S | 10/1995 | Savage et al. |
| 5,456,252 | A | 10/1995 | Vari et al. |
| 5,458,117 | A | 10/1995 | Chamoun et al. |
| 5,477,051 | A | 12/1995 | Tsuchiya |
| 5,479,934 | A | 1/1996 | Imran |
| 5,482,036 | A | 1/1996 | Diab et al. |
| 5,490,505 | A | 2/1996 | Diab et al. |
| 5,492,118 | A | 2/1996 | Gratton et al. |
| 5,494,043 | A | 2/1996 | O'Sullivan et al. |
| 5,497,769 | A | 3/1996 | Gratton et al. |
| 5,497,772 | A * | 3/1996 | Schulman ......... A61B 5/14865 204/403.09 |
| 5,511,552 | A | 4/1996 | Johnson |
| 5,517,987 | A | 5/1996 | Tsuchiya |
| 5,520,176 | A | 5/1996 | Cohen |
| 5,520,683 | A | 5/1996 | Subramaniam et al. |
| 5,529,065 | A | 6/1996 | Tsuchiya |
| 5,533,511 | A | 7/1996 | Kaspari et al. |
| 5,534,851 | A | 7/1996 | Russek |
| 5,540,722 | A | 7/1996 | Clare et al. |
| 5,553,614 | A | 9/1996 | Chance |
| 5,561,275 | A | 10/1996 | Savage et al. |
| 5,562,002 | A | 10/1996 | Lalin |
| 5,564,417 | A | 10/1996 | Chance |
| 5,564,418 | A | 10/1996 | Ozaki et al. |
| 5,582,169 | A | 12/1996 | Oda et al. |
| 5,590,649 | A | 1/1997 | Caro et al. |
| 5,596,038 | A | 1/1997 | Subramaniam |
| 5,596,987 | A | 1/1997 | Chance |
| 5,602,924 | A | 2/1997 | Durand et al. |
| 5,605,157 | A | 2/1997 | Panescu et al. |
| 5,626,145 | A | 5/1997 | Clapp et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,640,247 | A | 6/1997 | Tsuchiya et al. |
| 5,645,440 | A | 7/1997 | Tobler et al. |
| 5,664,574 | A | 9/1997 | Chance |
| 5,673,701 | A | 10/1997 | Chance |
| 5,676,142 | A | 10/1997 | Miwa et al. |
| 5,678,558 | A | 10/1997 | Johnson |
| 5,678,560 | A | 10/1997 | Sakamoto et al. |
| 5,685,299 | A | 11/1997 | Diab et al. |
| 5,686,516 | A | 11/1997 | Tzur |
| 5,694,931 | A | 12/1997 | Tsuchiya |
| 5,706,821 | A | 1/1998 | Matcher et al. |
| 5,727,547 | A | 3/1998 | Levinson et al. |
| D393,830 | S | 4/1998 | Tobler et al. |
| 5,743,260 | A | 4/1998 | Chung et al. |
| 5,743,262 | A | 4/1998 | Lepper, Jr. et al. |
| 5,746,210 | A | 5/1998 | Benaron et al. |
| 5,752,519 | A | 5/1998 | Benaron et al. |
| 5,752,914 | A | 5/1998 | Delonzor et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,772,587 | A | 6/1998 | Gratton et al. |
| 5,772,588 | A | 6/1998 | Miwa et al. |
| 5,775,330 | A | 7/1998 | Kangas et al. |
| 5,776,058 | A | 7/1998 | Levinson et al. |
| 5,779,631 | A | 7/1998 | Chance |
| 5,782,237 | A | 7/1998 | Casciani et al. |
| 5,782,756 | A | 7/1998 | Mannheimer |
| 5,782,757 | A | 7/1998 | Diab et al. |
| 5,785,658 | A | 7/1998 | Benaron et al. |
| 5,785,659 | A | 7/1998 | Caro et al. |
| 5,791,347 | A | 8/1998 | Flaherty et al. |
| 5,807,261 | A | 9/1998 | Benaron et al. |
| 5,807,263 | A | 9/1998 | Chance |
| 5,810,734 | A | 9/1998 | Caro et al. |
| 5,813,980 | A | 9/1998 | Levinson et al. |
| 5,813,993 | A | 9/1998 | Kaplan et al. |
| 5,816,247 | A | 10/1998 | Maynard |
| 5,820,558 | A | 10/1998 | Chance |
| 5,823,950 | A | 10/1998 | Diab et al. |
| 5,823,952 | A | 10/1998 | Levinson et al. |
| 5,830,131 | A | 11/1998 | Caro et al. |
| 5,833,618 | A | 11/1998 | Caro et al. |
| 5,846,208 | A | 12/1998 | Pichlmayr et al. |
| 5,851,179 | A | 12/1998 | Ritson et al. |
| 5,853,370 | A | 12/1998 | Chance et al. |
| RE36,044 | E | 1/1999 | Benaron |

(56) References Cited

U.S. PATENT DOCUMENTS

| | | | |
|---|---|---|---|
| 5,857,979 A | 1/1999 | Ryu et al. |
| 5,860,919 A | 1/1999 | Kiani-Azarbayjany et al. |
| 5,865,736 A | 2/1999 | Baker, Jr. et al. |
| 5,873,821 A | 2/1999 | Chance et al. |
| 5,879,294 A | 3/1999 | Anderson et al. |
| 5,890,929 A | 4/1999 | Mills et al. |
| 5,904,654 A | 5/1999 | Wohltmann et al. |
| 5,917,190 A | 6/1999 | Yodh et al. |
| 5,919,134 A | 7/1999 | Diab |
| 5,934,925 A | 8/1999 | Tobler et al. |
| 5,940,182 A | 8/1999 | Lepper, Jr. et al. |
| 5,954,053 A | 9/1999 | Chance et al. |
| 5,983,121 A | 11/1999 | Tsuchiya |
| 5,987,346 A | 11/1999 | Benaron et al. |
| 5,987,351 A | 11/1999 | Chance |
| 5,995,855 A | 11/1999 | Kiani et al. |
| 5,997,343 A | 12/1999 | Mills et al. |
| 5,999,846 A | 12/1999 | Pardey et al. |
| 6,002,952 A | 12/1999 | Diab et al. |
| 6,011,986 A | 1/2000 | Diab et al. |
| 6,011,990 A | 1/2000 | Schultz et al. |
| 6,027,452 A | 2/2000 | Flaherty et al. |
| 6,032,065 A | 2/2000 | Brown et al. |
| 6,035,223 A | 3/2000 | Baker, Jr. |
| 6,036,642 A | 3/2000 | Diab et al. |
| 6,045,509 A | 4/2000 | Caro et al. |
| 6,052,619 A * | 4/2000 | John .................... 600/544 |
| 6,058,324 A | 5/2000 | Chance |
| 6,067,462 A | 5/2000 | Diab et al. |
| 6,067,467 A | 5/2000 | John |
| 6,069,975 A | 5/2000 | Lehmann et al. |
| 6,070,098 A | 5/2000 | Moore-Ede et al. |
| 6,075,610 A | 6/2000 | Ueda et al. |
| 6,076,010 A | 6/2000 | Boas et al. |
| 6,078,833 A | 6/2000 | Hueber |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,154,669 A | 11/2000 | Hunter et al. |
| 6,157,850 A | 12/2000 | Diab et al. |
| 6,157,857 A | 12/2000 | Dimpfel |
| 6,165,005 A | 12/2000 | Mills et al. |
| 6,184,521 B1 | 2/2001 | Coffin, IV et al. |
| 6,192,260 B1 | 2/2001 | Chance |
| 6,192,261 B1 | 2/2001 | Gratton et al. |
| 6,206,830 B1 | 3/2001 | Diab et al. |
| 6,216,021 B1 | 4/2001 | Franceschini et al. |
| 6,229,856 B1 | 5/2001 | Diab et al. |
| 6,232,609 B1 | 5/2001 | Snyder et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,236,885 B1 | 5/2001 | Hunter et al. |
| 6,240,305 B1 | 5/2001 | Tsuchiya |
| 6,241,683 B1 | 6/2001 | Macklem et al. |
| 6,246,892 B1 | 6/2001 | Chance |
| 6,253,097 B1 | 6/2001 | Aronow et al. |
| 6,256,523 B1 | 7/2001 | Diab et al. |
| 6,263,221 B1 | 7/2001 | Chance et al. |
| 6,263,222 B1 | 7/2001 | Diab et al. |
| 6,272,363 B1 | 8/2001 | Casciani et al. |
| 6,272,367 B1 | 8/2001 | Chance |
| 6,272,378 B1 | 8/2001 | Baumgart-Schmitt |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,298,252 B1 | 10/2001 | Kovach et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,335,792 B1 | 1/2002 | Tsuchiya |
| 6,343,224 B1 | 1/2002 | Parker |
| 6,343,229 B1 | 1/2002 | Siebler et al. |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,377,840 B1 | 4/2002 | Gritsenko et al. |
| 6,385,486 B1 * | 5/2002 | John et al. .................... 600/544 |
| 6,388,240 B2 | 5/2002 | Schulz et al. |
| 6,397,091 B2 | 5/2002 | Diab et al. |
| 6,397,099 B1 | 5/2002 | Chance |
| 6,397,845 B1 | 6/2002 | Burton |
| 6,416,480 B1 | 7/2002 | Nenov |
| 6,430,437 B1 | 8/2002 | Marro |
| 6,430,525 B1 | 8/2002 | Weber et al. |
| 6,445,955 B1 * | 9/2002 | Michelson et al. ............. 607/46 |
| 6,456,862 B2 | 9/2002 | Benni |
| 6,463,310 B1 | 10/2002 | Swedlow et al. |
| 6,463,311 B1 | 10/2002 | Diab |
| 6,470,199 B1 | 10/2002 | Kopotic et al. |
| 6,473,632 B1 | 10/2002 | Myers |
| 6,481,899 B1 | 11/2002 | Quast et al. |
| 6,487,343 B1 | 11/2002 | Lewandowski et al. |
| 6,496,724 B1 | 12/2002 | Levendowski et al. |
| 6,497,658 B2 | 12/2002 | Roizen et al. |
| 6,501,975 B2 | 12/2002 | Diab et al. |
| 6,505,059 B1 | 1/2003 | Kollias et al. |
| 6,511,424 B1 | 1/2003 | Moore-Ede et al. |
| 6,515,273 B2 | 2/2003 | Al-Ali |
| 6,516,209 B2 | 2/2003 | Cheng et al. |
| 6,516,214 B1 | 2/2003 | Boas |
| 6,519,487 B1 | 2/2003 | Parker |
| 6,525,386 B1 | 2/2003 | Mills et al. |
| 6,526,300 B1 | 2/2003 | Kiani et al. |
| 6,526,309 B1 | 2/2003 | Chance |
| 6,537,228 B1 | 3/2003 | Lambert |
| 6,541,756 B2 | 4/2003 | Schulz et al. |
| 6,542,764 B1 | 4/2003 | Al-Ali et al. |
| 6,542,772 B1 | 4/2003 | Chance |
| 6,549,284 B1 | 4/2003 | Boas et al. |
| 6,564,076 B1 | 5/2003 | Chance |
| 6,567,165 B1 | 5/2003 | Tsuchiya et al. |
| 6,575,902 B1 | 6/2003 | Burton |
| 6,577,884 B1 | 6/2003 | Boas |
| 6,580,086 B1 | 6/2003 | Schulz et al. |
| 6,584,336 B1 | 6/2003 | Ali et al. |
| 6,587,703 B2 | 7/2003 | Cheng et al. |
| 6,591,123 B2 | 7/2003 | Fein et al. |
| 6,594,513 B1 | 7/2003 | Jobsis et al. |
| 6,594,518 B1 | 7/2003 | Benaron et al. |
| 6,595,316 B2 | 7/2003 | Cybulski et al. |
| 6,597,931 B1 | 7/2003 | Cheng et al. |
| 6,597,932 B2 | 7/2003 | Tian et al. |
| 6,597,933 B2 | 7/2003 | Kiani et al. |
| 6,599,281 B1 | 7/2003 | Struys et al. |
| 6,606,511 B1 | 8/2003 | Ali et al. |
| 6,609,024 B1 | 8/2003 | Ryu et al. |
| 6,618,614 B1 | 9/2003 | Chance |
| 6,631,291 B2 | 10/2003 | Viertio-Oja et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,654,632 B2 | 11/2003 | Lange et al. |
| 6,658,276 B2 | 12/2003 | Pishney et al. |
| 6,661,161 B1 | 12/2003 | Lanzo et al. |
| 6,662,033 B2 | 12/2003 | Casciani et al. |
| 6,665,560 B2 | 12/2003 | Becker et al. |
| 6,667,803 B1 | 12/2003 | Flessland et al. |
| 6,671,530 B2 | 12/2003 | Chung et al. |
| 6,671,531 B2 | 12/2003 | Al-Ali et al. |
| 6,675,031 B1 | 1/2004 | Porges et al. |

(56) References Cited

U.S. PATENT DOCUMENTS

| | | | |
|---|---|---|---|
| 6,678,543 B2 | 1/2004 | Diab et al. |
| 6,684,090 B2 | 1/2004 | Ali et al. |
| 6,684,091 B2 | 1/2004 | Parker |
| 6,687,524 B1 | 2/2004 | Svejk |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,048 B1 | 3/2004 | Chance |
| 6,708,049 B1 | 3/2004 | Berson et al. |
| 6,711,426 B2 | 3/2004 | Benaron et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,728,564 B2 | 4/2004 | Lahteenmaki |
| 6,731,975 B1 | 5/2004 | Viertio-Oja |
| 6,735,458 B2 | 5/2004 | Cheng et al. |
| 6,735,459 B2 | 5/2004 | Parker |
| 6,745,060 B2 | 6/2004 | Diab et al. |
| 6,748,259 B1 | 6/2004 | Benaron et al. |
| 6,748,263 B2 | 6/2004 | Griffiths et al. |
| 6,751,499 B2 | 6/2004 | Lange et al. |
| 6,757,558 B2 | 6/2004 | Lange et al. |
| 6,760,607 B2 | 7/2004 | Al-All |
| 6,768,920 B2 | 7/2004 | Lange et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,795,724 B2 | 9/2004 | Hogan |
| 6,801,648 B2 | 10/2004 | Cheng |
| 6,801,797 B2 | 10/2004 | Mannheimer et al. |
| 6,801,803 B2 | 10/2004 | Viertio-Oja |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,047 B2 | 12/2004 | Heitmeier et al. |
| 6,830,711 B2 | 12/2004 | Mills et al. |
| 6,836,502 B2 | 12/2004 | Canady et al. |
| 6,839,583 B1 | 1/2005 | Lewandowski et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,892,006 B2 | 5/2005 | Lewandowski et al. |
| 6,898,452 B2 | 5/2005 | Al-Ali et al. |
| 6,907,280 B2 | 6/2005 | Becerra et al. |
| 6,920,345 B2 | 7/2005 | Al-Ali et al. |
| 6,931,268 B1 | 8/2005 | Kiani-Azarbayjany et al. |
| 6,934,570 B2 * | 8/2005 | Kiani et al. ................... 600/324 |
| 6,934,579 B2 | 8/2005 | Mantzxaridis et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,950,698 B2 | 9/2005 | Sarkela et al. |
| 6,956,650 B2 | 10/2005 | Boas et al. |
| 6,958,815 B2 | 10/2005 | Bevilacqua et al. |
| 6,961,598 B2 | 11/2005 | Diab |
| 6,970,792 B1 | 11/2005 | Diab |
| 6,975,901 B2 | 12/2005 | Philip |
| 6,979,812 B2 | 12/2005 | Al-Ali |
| 6,985,763 B2 | 1/2006 | Boas et al. |
| 6,985,764 B2 | 1/2006 | Mason et al. |
| 6,993,371 B2 | 1/2006 | Kiani et al. |
| 6,993,380 B1 | 1/2006 | Modarres |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,010,341 B2 | 3/2006 | Chance |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,744 B2 | 4/2006 | Cheriet et al. |
| 7,039,449 B2 | 5/2006 | Al-Ali |
| 7,041,060 B2 | 5/2006 | Flaherty et al. |
| 7,044,918 B2 | 5/2006 | Diab |
| 7,047,054 B2 | 5/2006 | Benni |
| 7,047,055 B2 | 5/2006 | Boas et al. |
| 7,047,056 B2 | 5/2006 | Hannula et al. |
| 7,054,680 B1 | 5/2006 | Genger et al. |
| 7,067,893 B2 | 6/2006 | Mills et al. |
| 7,072,701 B2 | 7/2006 | Chen et al. |
| 7,085,597 B2 | 8/2006 | Fein et al. |
| 7,092,748 B2 | 8/2006 | Valdes et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,139,603 B2 | 11/2006 | Chance |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,209,861 B2 | 4/2007 | Hively |
| 7,215,984 B2 | 5/2007 | Diab |
| 7,215,986 B2 | 5/2007 | Diab |
| 7,220,240 B2 | 5/2007 | Struys et al. |
| 7,221,971 B2 | 5/2007 | Diab |
| 7,221,975 B2 | 5/2007 | Lindstrom |
| 7,225,006 B2 | 5/2007 | Al-Ali et al. |
| 7,225,007 B2 | 5/2007 | Al-Ali |
| 7,225,013 B2 | 5/2007 | Geva et al. |
| RE39,672 E | 6/2007 | Shehada et al. |
| 7,228,169 B2 | 6/2007 | Viertio-Oja |
| 7,229,430 B2 | 6/2007 | Hickle et al. |
| 7,231,246 B2 | 6/2007 | Rautee et al. |
| 7,239,385 B2 | 7/2007 | Schmitz et al. |
| 7,239,901 B2 | 7/2007 | Gritsenko |
| 7,239,905 B2 | 7/2007 | Kiani-Azarbayjany et al. |
| 7,239,988 B2 | 7/2007 | Hasson et al. |
| 7,245,953 B1 | 7/2007 | Parker |
| 7,248,909 B2 | 7/2007 | Lee et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,254,500 B2 | 8/2007 | Makeig et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,277,741 B2 | 10/2007 | Debreczeny et al. |
| 7,277,831 B1 | 10/2007 | Pawelzik et al. |
| 7,280,858 B2 | 10/2007 | Al-Ali et al. |
| 7,288,066 B2 | 10/2007 | Drew |
| 7,289,835 B2 | 10/2007 | Mansfield et al. |
| 7,289,837 B2 | 10/2007 | Mannheimer et al. |
| 7,292,883 B2 | 11/2007 | De Felice et al. |
| 7,295,866 B2 | 11/2007 | Al-Ali |
| 7,313,427 B2 | 12/2007 | Benni |
| 7,328,053 B1 | 2/2008 | Diab et al. |
| 7,332,784 B2 | 2/2008 | Mills et al. |
| 7,333,647 B2 | 2/2008 | Boas et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,343,187 B2 | 3/2008 | Stetson |
| 7,349,726 B2 | 3/2008 | Casciani et al. |
| D566,282 S | 4/2008 | Al-Ali et al. |
| 7,355,512 B1 | 4/2008 | Al-Ali |
| 7,355,688 B2 | 4/2008 | Lash et al. |
| 7,356,365 B2 | 4/2008 | Schurman |
| D568,479 S | 5/2008 | Mao et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,373,198 B2 | 5/2008 | Bibian et al. |
| 7,376,453 B1 | 5/2008 | Diab et al. |
| 7,376,454 B2 | 5/2008 | Casciani et al. |

(56) References Cited

U.S. PATENT DOCUMENTS

| | | | |
|---|---|---|---|
| 7,377,794 B2 | 5/2008 | Al-Ali et al. |
| 7,377,899 B2 | 5/2008 | Weber et al. |
| 7,383,070 B2 | 6/2008 | Diab et al. |
| 7,392,074 B2 | 6/2008 | Isaacson et al. |
| 7,415,297 B2 | 8/2008 | Al-Ali et al. |
| 7,415,298 B2 | 8/2008 | Casciani et al. |
| 7,427,165 B2 | 9/2008 | Benaron et al. |
| 7,428,432 B2 | 9/2008 | Ali et al. |
| 7,428,434 B2 | 9/2008 | Tromberg et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,457,652 B2 | 11/2008 | Porges et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,471,978 B2 * | 12/2008 | John et al. ............ 600/544 |
| 7,474,245 B1 | 1/2009 | Wang et al. |
| 7,478,108 B2 | 1/2009 | Townsend et al. |
| 7,483,729 B2 | 1/2009 | Al-Ali et al. |
| 7,483,730 B2 | 1/2009 | Diab et al. |
| 7,483,731 B2 | 1/2009 | Hoarau et al. |
| 7,489,958 B2 | 2/2009 | Diab et al. |
| 7,496,391 B2 | 2/2009 | Diab et al. |
| 7,496,393 B2 | 2/2009 | Diab et al. |
| 7,496,400 B2 | 2/2009 | Hoskonen et al. |
| D587,657 S | 3/2009 | Al-Ali et al. |
| 7,499,740 B2 | 3/2009 | Nordstrom et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,948 B1 | 4/2009 | Balberg et al. |
| 7,522,949 B2 | 4/2009 | Berson et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,610,082 B2 | 10/2009 | Chance |
| 7,618,375 B2 | 11/2009 | Flaherty |
| D606,659 S | 12/2009 | Kiani et al. |
| 7,632,148 B1 * | 12/2009 | Kawamura ........ H01R 13/5221 439/607.41 |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,108,039 B2 * | 1/2012 | Saliga et al. ............ 600/544 |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |

(56) References Cited

U.S. PATENT DOCUMENTS

| | | |
|---|---|---|
| 8,457,707 B2 | 6/2013 | Kiani |
| 8,463,349 B2 | 6/2013 | Diab et al. |
| 8,466,286 B2 | 6/2013 | Bellott et al. |
| 8,467,880 B2 * | 6/2013 | Glukhovsky et al. ......... 607/48 |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,660,489 B2 * | 2/2014 | Barrenscheen ...... H04B 5/0031 375/258 |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |

(56) References Cited

U.S. PATENT DOCUMENTS

| | | | |
|---|---|---|---|
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 2002/0019588 A1 | 2/2002 | Marro et al. |
| 2002/0029005 A1 | 3/2002 | Levendowski et al. |
| 2002/0082513 A1 | 6/2002 | Ennen et al. |
| 2002/0085174 A1 | 7/2002 | Bolger et al. |
| 2002/0123693 A1 | 9/2002 | Lange et al. |
| 2002/0183634 A1 | 12/2002 | Rantala et al. |
| 2002/0188216 A1 | 12/2002 | Kayyali et al. |
| 2002/0193844 A1* | 12/2002 | Michelson et al. | 607/48 |
| 2003/0069516 A1 | 4/2003 | Becker et al. |
| 2003/0145854 A1 | 8/2003 | Hickle |
| 2003/0158587 A1 | 8/2003 | Esteller et al. |
| 2003/0204148 A1 | 10/2003 | Lange et al. |
| 2003/0225323 A1* | 12/2003 | Kiani et al. | 600/323 |
| 2004/0056103 A1* | 3/2004 | Sepponen | 235/487 |
| 2004/0073098 A1 | 4/2004 | Geva et al. |
| 2004/0073129 A1 | 4/2004 | Caldwell et al. |
| 2004/0082876 A1 | 4/2004 | Viertio-Oja et al. |
| 2004/0167418 A1 | 8/2004 | Nguyen et al. |
| 2004/0193068 A1 | 9/2004 | Burton et al. |
| 2004/0243017 A1 | 12/2004 | Causevic |
| 2004/0267153 A1 | 12/2004 | Bergethon |
| 2005/0010116 A1 | 1/2005 | Korhonen et al. |
| 2005/0059899 A1 | 3/2005 | Merilainen et al. |
| 2005/0081847 A1 | 4/2005 | Lee et al. |
| 2005/0090754 A1 | 4/2005 | Wolff et al. |
| 2005/0113704 A1 | 5/2005 | Lawson et al. |
| 2005/0119547 A1 | 6/2005 | Shastri et al. |
| 2005/0217674 A1 | 10/2005 | Burton et al. |
| 2005/0277826 A1* | 12/2005 | Dunseath, Jr. | 600/410 |
| 2006/0100538 A1 | 5/2006 | Genger et al. |
| 2006/0116556 A1 | 6/2006 | Duhamel |
| 2006/0167368 A1 | 7/2006 | Sarkela |
| 2006/0189861 A1 | 8/2006 | Chen et al. |
| 2006/0217628 A1 | 9/2006 | Huiku |
| 2006/0235315 A1 | 10/2006 | Akselrod |
| 2006/0241356 A1 | 10/2006 | Flaherty |
| 2006/0241562 A1 | 10/2006 | John et al. |
| 2006/0293608 A1 | 12/2006 | Rothman et al. |
| 2007/0010755 A1 | 1/2007 | Sarkela et al. |
| 2007/0010756 A1 | 1/2007 | Viertio-Oja |
| 2007/0010795 A1 | 1/2007 | Sarkela et al. |
| 2007/0173802 A1* | 7/2007 | Keppel | 606/34 |
| 2007/0185407 A1 | 8/2007 | Xu et al. |
| 2007/0208269 A1* | 9/2007 | Mumford et al. | 600/546 |
| 2007/0244721 A1 | 10/2007 | Sackner-Bernstein et al. |
| 2007/0249952 A1 | 10/2007 | Rubin et al. |
| 2008/0017800 A1 | 1/2008 | Benni |
| 2008/0234597 A1 | 9/2008 | Becker et al. |
| 2008/0255469 A1 | 10/2008 | Shieh et al. |
| 2008/0285029 A1 | 11/2008 | Benni et al. |
| 2008/0294063 A1 | 11/2008 | Bibian et al. |
| 2008/0300469 A1 | 12/2008 | Kuo et al. |
| 2008/0300473 A1 | 12/2008 | Benni |
| 2008/0300474 A1 | 12/2008 | Benni et al. |
| 2008/0312523 A1* | 12/2008 | Dunseath | 600/383 |
| 2009/0018427 A1 | 1/2009 | Causevic et al. |
| 2009/0018429 A1 | 1/2009 | Saliga et al. |
| 2009/0036799 A1 | 2/2009 | Sandhu et al. |
| 2009/0108205 A1 | 4/2009 | Duffy et al. |
| 2009/0182209 A1 | 7/2009 | Benni |
| 2009/0247984 A1 | 10/2009 | Lamego et al. |
| 2009/0275844 A1 | 11/2009 | Al-Ali |
| 2009/0281403 A1 | 11/2009 | Benni |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0049018 A1 | 2/2010 | Duffy et al. |
| 2010/0144164 A1* | 6/2010 | Wang | H01R 13/6205 439/39 |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0189952 A1* | 8/2011 | Barrenscheen | H04B 5/0031 455/41.1 |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |

(56) References Cited

U.S. PATENT DOCUMENTS

| | | |
|---|---|---|
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |

FOREIGN PATENT DOCUMENTS

| | | | |
|---|---|---|---|
| EP | 638193 | 2/1995 | |
| EP | 1250886 | 10/2002 | |
| EP | 1624798 | 11/2004 | |
| EP | 1779257 | 5/2007 | |
| WO | WO 91/09372 | 6/1991 | |
| WO | WO 91/19453 | 12/1991 | |
| WO | WO 92/02176 | 2/1992 | |
| WO | WO 93/21615 | 10/1993 | |
| WO | WO 99/08589 | 2/1999 | |
| WO | WO 00/21435 | 4/2000 | |
| WO | WO 00/56211 | 9/2000 | |
| WO | WO 00/56212 | 9/2000 | |
| WO | WO 01/30414 | 5/2001 | |
| WO | WO 00/21432 | 4/2002 | |
| WO | WO 2004/028362 | 4/2004 | |
| WO | WO 2004038890 A1 * | 5/2004 | ............... H02J 7/02 |
| WO | WO 2004/054441 | 7/2004 | |
| WO | WO 2007/059248 | 5/2007 | |
| WO | WO 2007/140535 | 12/2007 | |
| WO | WO 2007/140536 | 12/2007 | |
| WO | WO 2007/149553 | 12/2007 | |
| WO | WO 2008/015449 | 2/2008 | |
| WO | WO 2008/040846 | 4/2008 | |
| WO | WO 2008/043365 | 4/2008 | |
| WO | WO 2008/109694 | 9/2008 | |
| WO | WO 2008/109699 | 9/2008 | |
| WO | WO 2008/119029 | 10/2008 | |
| WO | WO 2008/119031 | 10/2008 | |
| WO | WO 2008/122082 | 10/2008 | |
| WO | WO 2008/138340 | 11/2008 | |

OTHER PUBLICATIONS

Partial International Search Report for International Application No. PCT/US2011/053540, date of mailing: Jan. 30, 2012, in 4 pages.

International Search Report for International Application No. PCT/US2011/053540, date of mailing: May 3, 2012, in 14 pages.

* cited by examiner

MAGNETIC ELECTRICAL CONNECTOR FOR PATIENT MONITORS

PRIORITY CLAIM

This application claims the benefit of priority under 35 U.S.C. §119(e) of the following U.S. Provisional Patent Application No. 61/387,426, titled "Magnetic Electrical Connector For Patient Monitors," filed on Sep. 28, 2010, and incorporates that application by reference herein in its entirety.

REFERENCE TO RELATED APPLICATIONS

This application is related to U.S. Provisional Patent Application No. 61/387,457, titled "Depth of Consciousness Monitor Including Oximeter," filed on Sep. 28, 2010, and incorporates that application by reference herein in its entirety.

FIELD OF THE DISCLOSURE

The present disclosure relates to the field of patient monitoring devices. More specifically, the disclosure relates to electrical connectors for patient monitors adapted to measure blood analyses through optical noninvasive sensors.

BACKGROUND OF THE DISCLOSURE

Electric potentials evoked within a living subject are often sensed with electrodes or assemblies of multiple electrodes placed on the surface of a subject's or patient's body. In many clinical applications, the electric potentials acquired by the electrodes are processed, displayed, and/or recorded by instruments located remotely from the body. In such cases, the electrodes or electrode assemblies communicate with the remote instruments through connecting wires and cables of suitable length from the subject to the instrument.

While the foregoing electrodes are frequently designed to be disposable after use on a single subject, the cables and wires are generally intended to be reused multiple times. The electrodes often include terminals, connectors, or similar assemblies by which they can be detachably connected to the wires and/or cables. The contact surfaces at the points of connection may be subject to contamination, corrosion, or the like, they may cause unreliable connections, or degrade the quality of the bioelectric potentials, which are usually of very low voltage levels. The foregoing connections also may be subject to the ingress of fluids and any fluids entering a connector may degrade its performance. Additionally, many electrical connectors include traditional male and female mechanically matable components where at least one side often includes a cavity, recess, or the like. The cavity or recessed mechanical structures may trap biological contaminants making cleaning and sterilization difficult. Such difficulties may be exacerbated if the cable or wire is used on multiple subjects.

In addition to the foregoing, cables and wires leading from the patient to an instrument also present technical challenges regarding signal integrity. The capacitance between the wires of a given cable may present an undesirable electrical loading on the electrodes. Also, when flexed, cables may evoke triboelectric potentials, which may interfere with the signals of interest. Moreover, cables or wire may pick up electromagnetic interference, which may also degrade the signals of interest.

Often, for safety and signal integrity reasons, an instrument which acquires the electrode potentials generally has its inputs electrically isolated from ground, as well as from other circuits which may contact other parts of the subject. However, a long cable may create significant capacitance to ground, as well as to adjacent cables, at least in part defeating that isolation. The foregoing may lead to signal degradation, often in the form or reduced common-mode rejection. This drawback may be exacerbated where electrosurgical and related RF devices are employed in a subject.

Embodiments of the present disclosure seek to overcome some or all of these and other problems.

SUMMARY OF THE DISCLOSURE

Based on at least the foregoing, the present disclosure seeks to overcome some or all of the drawbacks discussed above and provide additional advantages over any prior technologies. For example, some or all of the foregoing drawbacks may advantageously be mitigated by signal isolation very near the electrodes, such that the electrodes are buffered and/or isolated from the effects of the cable and wiring. In general, designers of electrical components will recognize from the disclosure herein several modalities that accomplish electric signal isolation, including for example, magnetic, optical, or radiofrequency links, and capacitive coupling. An example of magnetic isolation is a transformer having primary and secondary windings separated by an insulating barrier. An optocoupler is an example of an optical isolation device, in which light from an intensity-modulated source passes through an insulating barrier and impinges on a photodetector, which recovers the original modulating signal. A modulated radio transmitter and demodulating receiver are still another example of a signal isolation device.

In an embodiment where the physical separation is large compared to a wavelength of the radio frequency, electromagnetic wave propagation is an operative coupling mechanism. In an embodiment where the transmitter and receiver are located in very close proximity, near-field coupling may be operative. In an embodiment, near-field coupling may be established magnetically by coils having mutual inductance yet insulated from each other, or may be established electrostatically by a small capacitance present across an insulating barrier between the transmitter and receiver circuits. A designer will recognize from the disclosure herein still and other methods. In an embodiment, the near field coupling mechanisms may also be used in conjunction with designs which are not strictly radiofrequency carriers. For example, the ISO721 and related devices, manufactured by Texas Instruments of Dallas, Tex., transmit digital signals across an insulating barrier by means of sensing pulse edges coupled through the tiny capacitance existing across the barrier.

In an embodiment, a device designer can use signal isolation to potentially establish a point of physical disconnection at the location of the insulating barrier. This may allow the designer to create an electrical connector with fewer or no exposed conductive parts. For example, in an embodiment, a transformer may have appropriate electrical characteristics to couple with the signal provided by a pair of electrodes on a subject's body. In an embodiment, the primary winding of this transformer may advantageously be a disposable electrode assembly placed near or on a patient. The cable leading to the instrument could be equipped with a secondary coil. Connection of the cable to the electrode assembly would be accomplished by bringing the coils into physical proximity, such that they are magnetically coupled, forming a transformer. It is noteworthy that this connection may have fewer or no exposed conductive parts, may be made immune or resistant to the ingress of liquids, and may be designed to be free from small cavities that would entrap biological materials, each reducing the risk of contamination and improving the efficiency and effectiveness of sterilization and signal coupling.

In an embodiment, a device designer can use a system for isolation of electrical components of a physiological monitoring system that comprises a sensor for detecting an indication of a physiological parameter, a patient monitoring system for displaying information transmitted from the sensor, an instrument cable connecting the sensor and the patient monitoring system, a sensor cable connecting the sensory components of the sensor to the instrument cable and a signal isolation coupling located along the sensor cable. This system could utilize an EEG sensor, a pulse oximeter, or a combination cerebral oximeter and EEG forehead sensor. The EEG forehead sensor may include a disposable portion that contains an EEG electrode cable connecting a set of EEG electrodes to the sensor cable. The EEG electrode cable may include a signal isolation coupling which may include an insulating barrier, or inductive components, for example, transformers. In some embodiments, the cerebral oximeter may be reusable.

A device designer may use a forehead sensor for isolation of electrical components of the sensor that includes at least one sensory component for detecting an indication of a physiological parameter of a patient, a sensor cable connected to the at least one sensory component for providing power and communication to the at least one sensory component, and a signal isolation coupling along the sensor cable. The at least one sensory component may be a plurality of EEG electrodes, a cerebral oximeter or pulse oximeter.

In an embodiment, a device designer can use a combination cerebral oximeter and EEG forehead sensor for isolation of electrical components that includes a reusable portion containing cerebral oximetry sensory components capable of detecting the cerebral oxygenation of matter inside the cerebral cavity, a disposable portion containing EEG electrodes capable of detecting electrical activity on a patient's skin, a disposable cable connecting the EEG electrodes to the reusable portion, and a signal isolation coupling connecting the disposable cable to the reusable portion. The sensor's signal isolation coupling may completely surround the signal isolation coupling to allow easy cleaning of the signal isolation coupling.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

The drawings are provided to illustrate embodiments of the disclosures described herein and do not limit the scope thereof.

FIGS. 3A-3B illustrate a cross-sectional view of an embodiment of the signal isolation coupling including a transformer and separation barriers, according to the present disclosure. FIGS. 3C-3E illustrate various circuit diagrams of an embodiment of the signal isolation coupling including a transformer, according to the present disclosure.

DETAILED DESCRIPTION OF THE PREFERRED EMBODIMENT

The present disclosure is generally related to signal couplings. In an embodiment, in order to provide an electrical coupling with fewer exposed conductors, and which reduces the ingress of liquids and entrapment of biological materials, an isolation connection is provided utilizing inductance and a physical gap between the conductors of the coupling. In an embodiment, a variety of medical devices could utilize a signal isolation connection between, among other places a sensor or other component interacting with a patient's body and the main instrument. For example, a device designer could implement a signal isolation component between a pulse oximeter and pulse oximetry sensor, an electroencephalogram "EEG" and the EEG electrodes, an electrocardiograph "ECG" and the ECG electrodes, acoustic throat sensors and a respiratory monitor, a temperature probe and a thermometer, and other medical devices with elements that come into close contact with a patient's body.

Figure 1A:
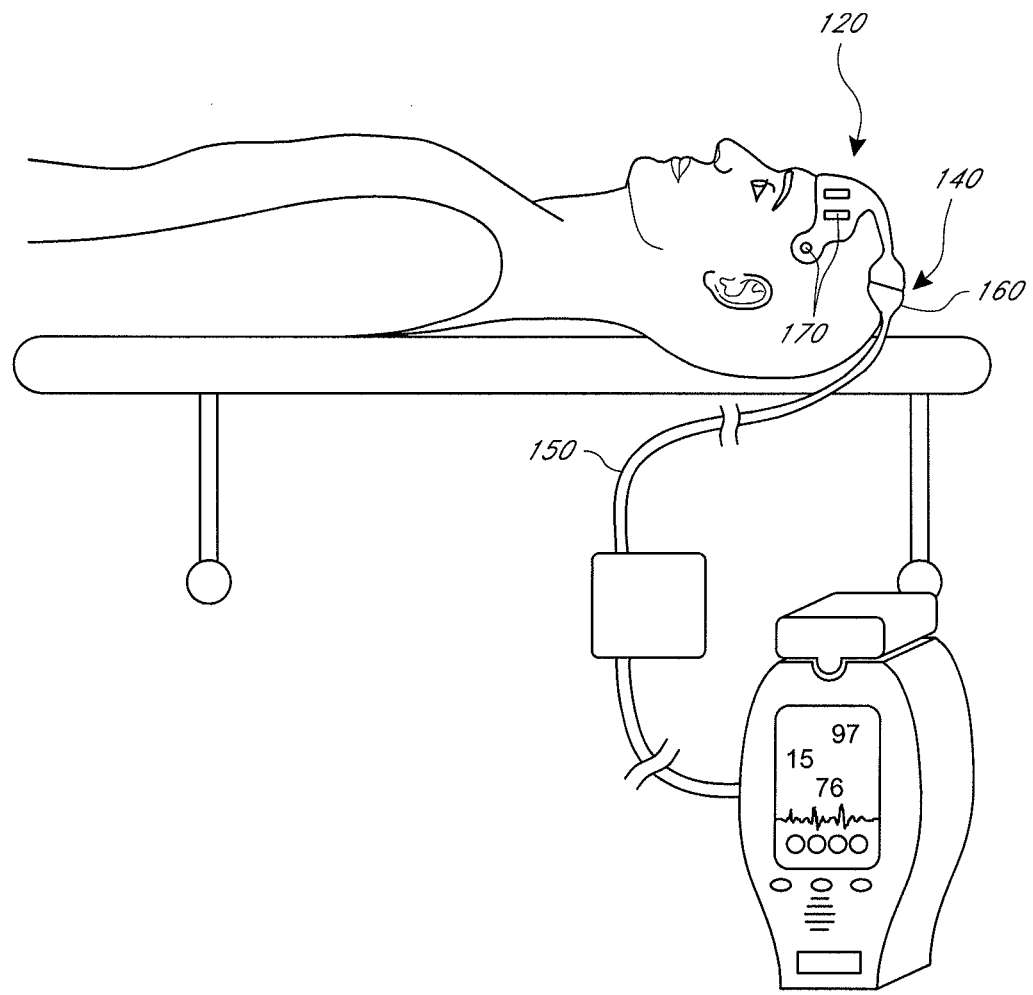
FIG. 1A-1E illustrate various patient monitoring devices communicating with optical sensors over cabling and through connections where signal isolation is preferred, according to embodiments of the present disclosure.
Figure 1B:
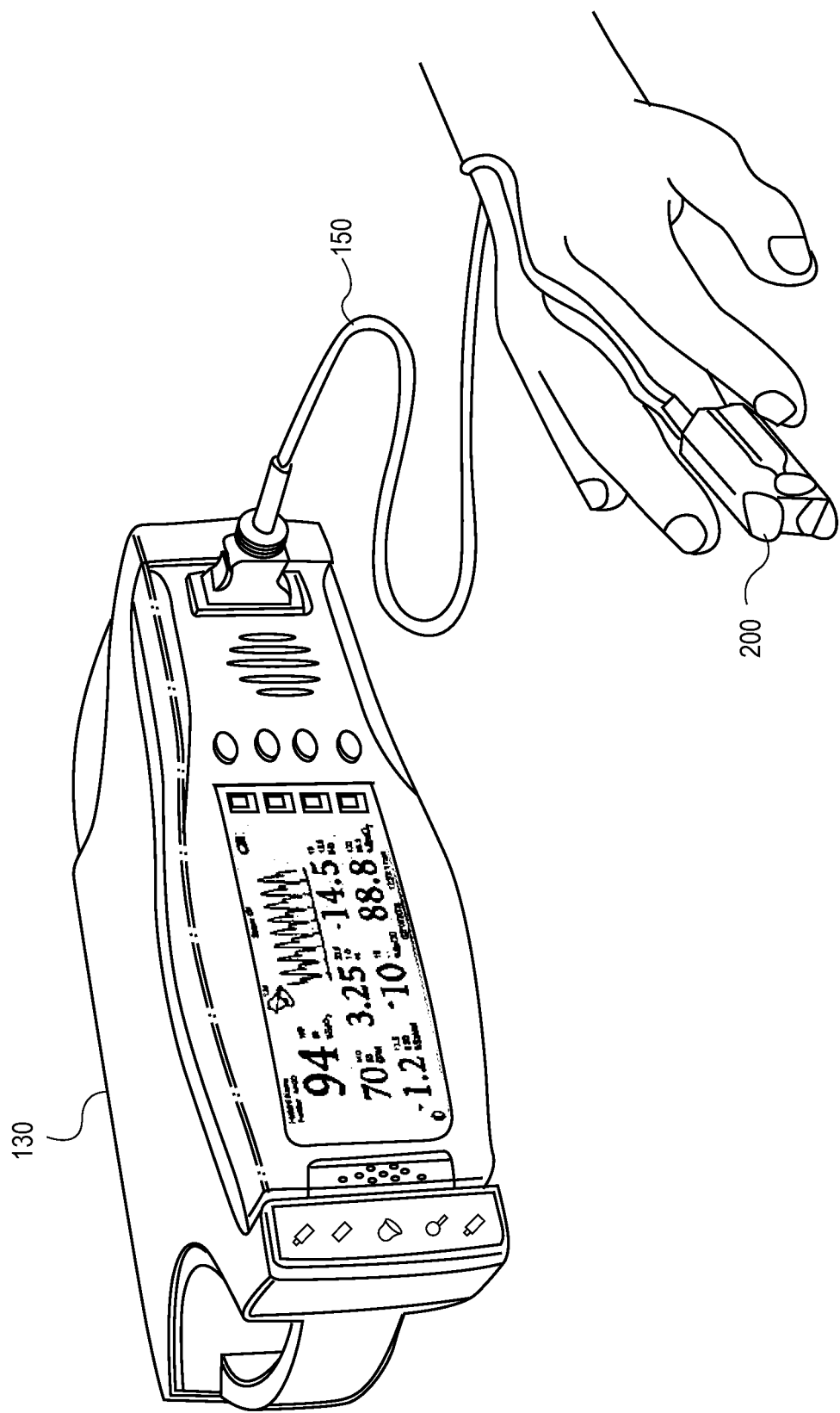
Figure 1C:
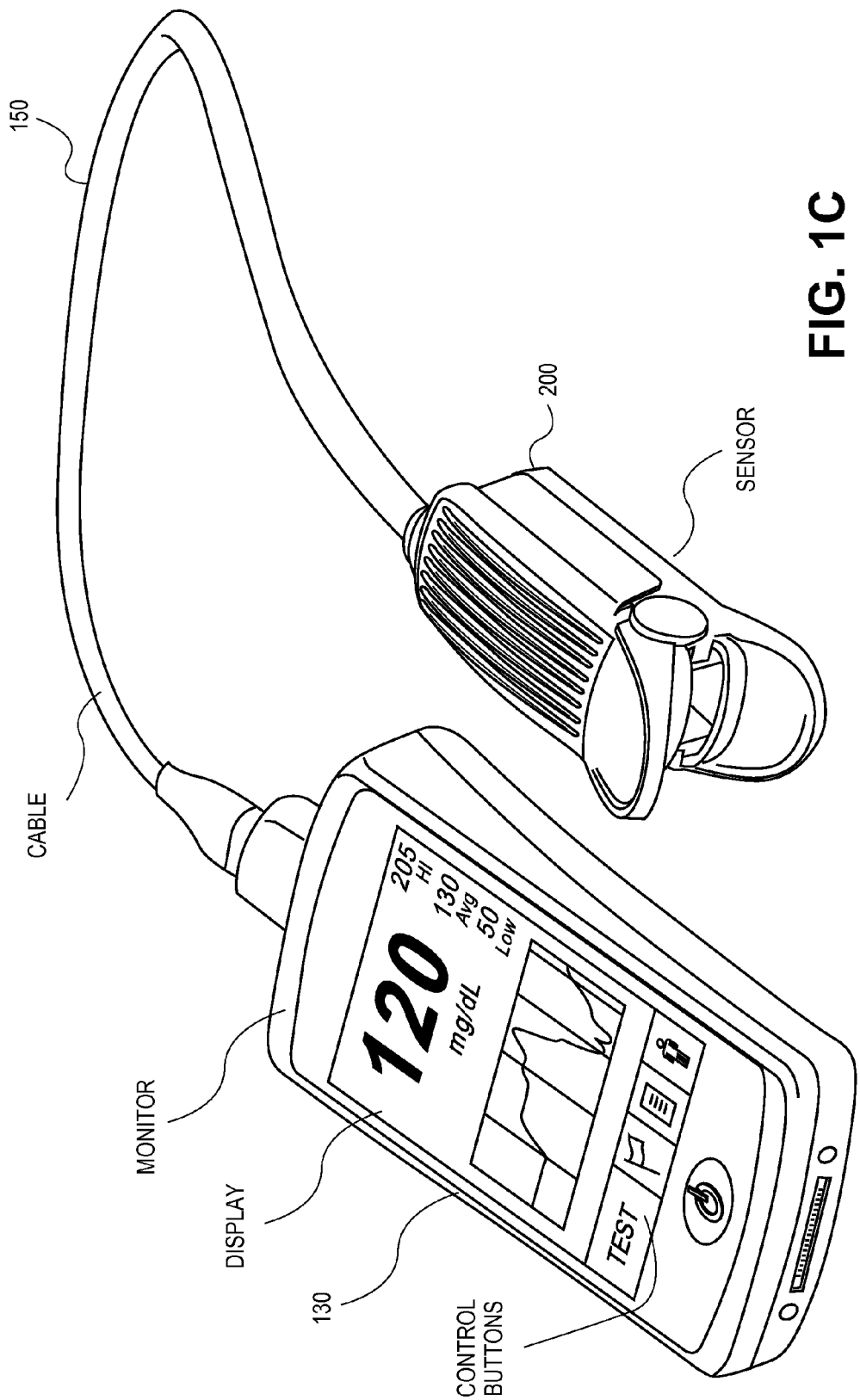
Figure 1D:
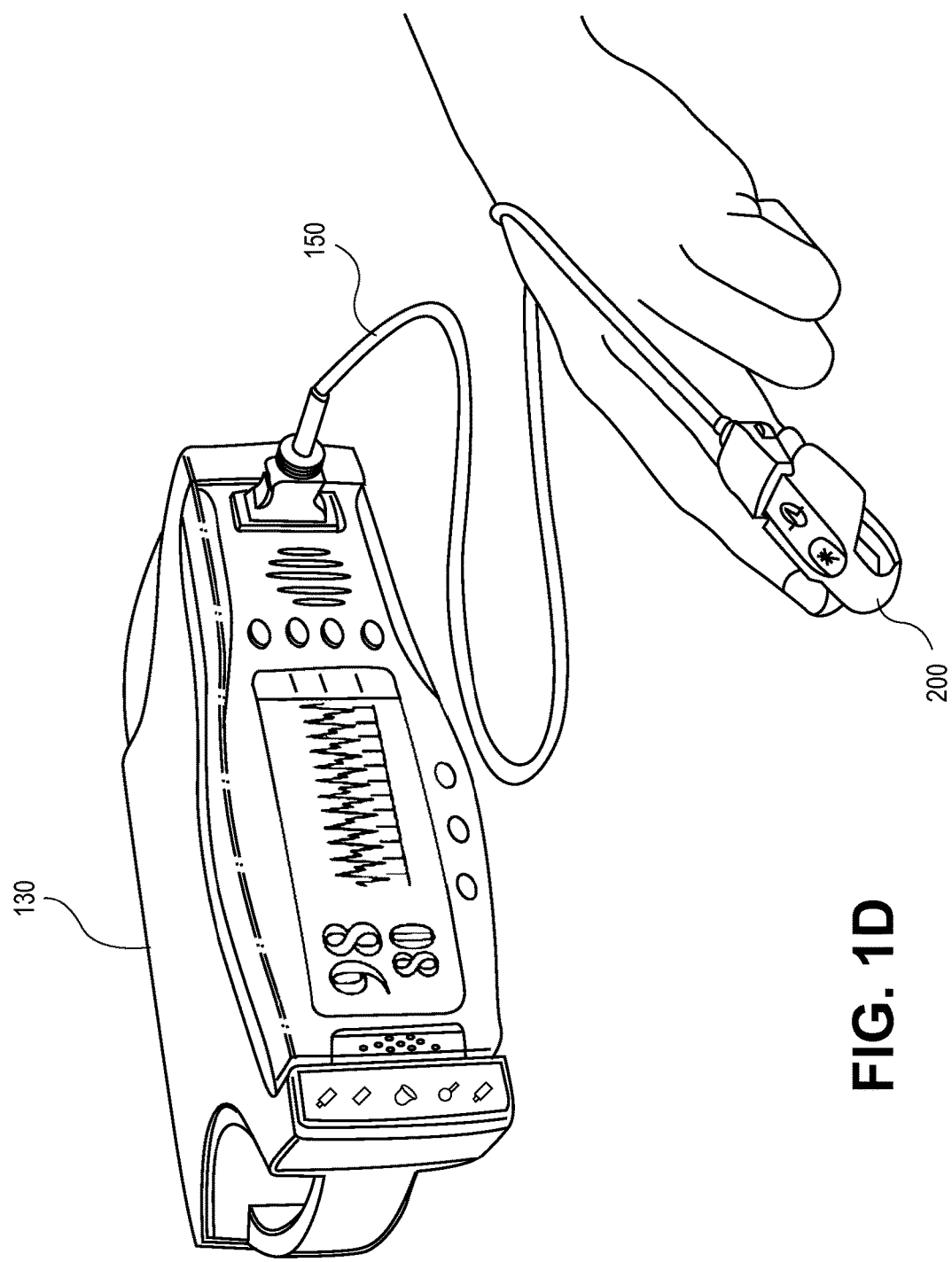
Figure 1E:
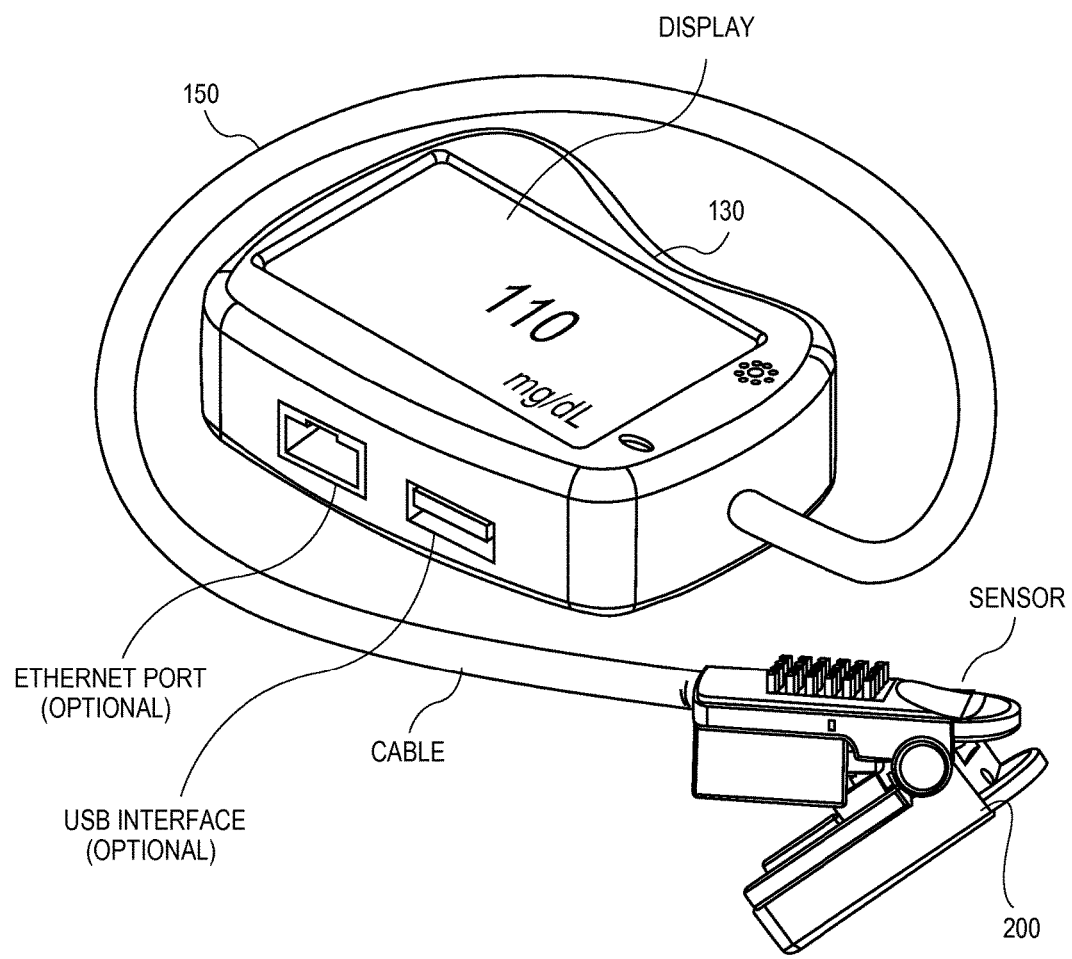

FIGS. 1A-1E illustrate various embodiments of medical devices that may incorporate a signal isolation coupling as disclosed herein. FIG. 1A illustrates an embodiment of a combination cerebral oximeter and EEG forehead sensor 120 connected by an instrument cable 150 to a conventional pulse oximeter 130. In this embodiment, a signal isolation coupling 140 could be implemented along the instrument cable 150, between the connection of the forehead sensor to the sensor cable 160 and the patient electrodes and sensors 170, or the like.

In an embodiment, the combination EEG and cerebral oximetry forehead sensor 120 may utilize both disposable and reusable components. For example, the disposable portion may advantageously include components near a measurement site surface (the patient's skin), including, for example, an EEG, a temperature sensor, tape, adhesive elements, positioning elements, or the like. The reusable portion may advantageously include more expensive or other components, circuitry and/or electronics. Although the reusable portion may still include time-of-use restrictions for quality control, it may be used multiple times for a single patient, across different patients, or the like. The reusable components may include, for example, cerebral oximetry components, pulse oximetry components and other components to measure other various parameters.

In an embodiment, the connection that connects the disposable portion and the reusable portion of the sensor 120 may be a signal isolation coupling 140 (as shown in FIGS. 3-7) as disclosed herein. The signal isolation coupling 140 (as shown in FIGS. 3-7) could be implemented at any point along either or both of a cable 150 connected to the disposable portion of the sensor 120 and/or a cable 150 connected to a reusable portion of the sensor 120. In one embodiment, the disposable portion of the sensor 120 has a cable 150 connected to it, which in turn has an isolation coupling 140 (as shown in FIGS. 3-7) that connects or communicates with a second cable 150 connected to the reusable portion of the sensor 120. The connection on the cable 150 connected to the reusable portion of the sensor 120 could be at any location along the cable 150 including the connection with the reusable portion of the sensor 120 or the connection to a main cable 150 that interfaces with a medical instrument, such as, for example, an oximter, a respiration monitor, a blood pressure monitor, or the like.

In an embodiment, a portion of the sensor 120 may communicate with or transmit power with another portion of the sensor 120 or any wire or other electrical connection leading to the signal processing and conditioning unit 190 through a signal isolation coupling 140 (as shown in FIGS. 3-7) as disclosed herein. In an embodiment, the signal isolation coupling 140 (as shown in FIGS. 3-7) could include an inductance connection with transformers embedded near the surface of each half of the connector that are housed by an insulator, for example, plastic. In an embodiment, the two halves of the connector could then be brought in close contact and be removably connected in place to provide a data communication, power connection, or the like.

FIGS. 1B-1E illustrate various additional embodiments of monitoring devices utilizing a finger clip sensor 200 and an instrument, such as, for example, a pulse oximeter 130. In an embodiment, a signal isolation coupling 140 (as shown in FIGS. 3-7) may be implemented in these embodiments in various places along an instrument cable 150 connecting the sensor 120 to the instrument, or in other positions.

Figure 2A:
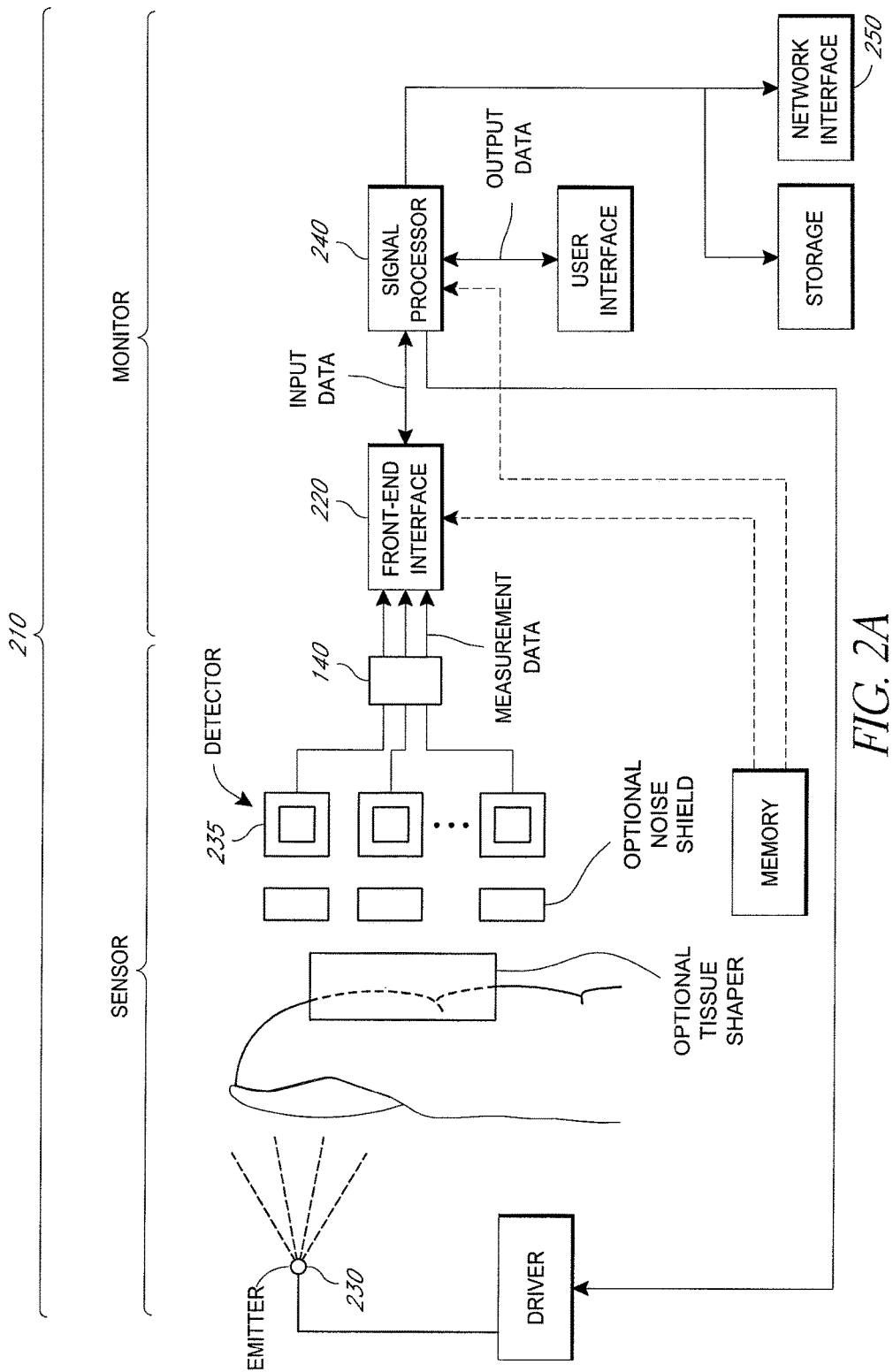
FIG. 2A illustrates a simplified block diagram of an embodiment of a pulse oximetry unit, according to the present disclosure.
Figure 2B:
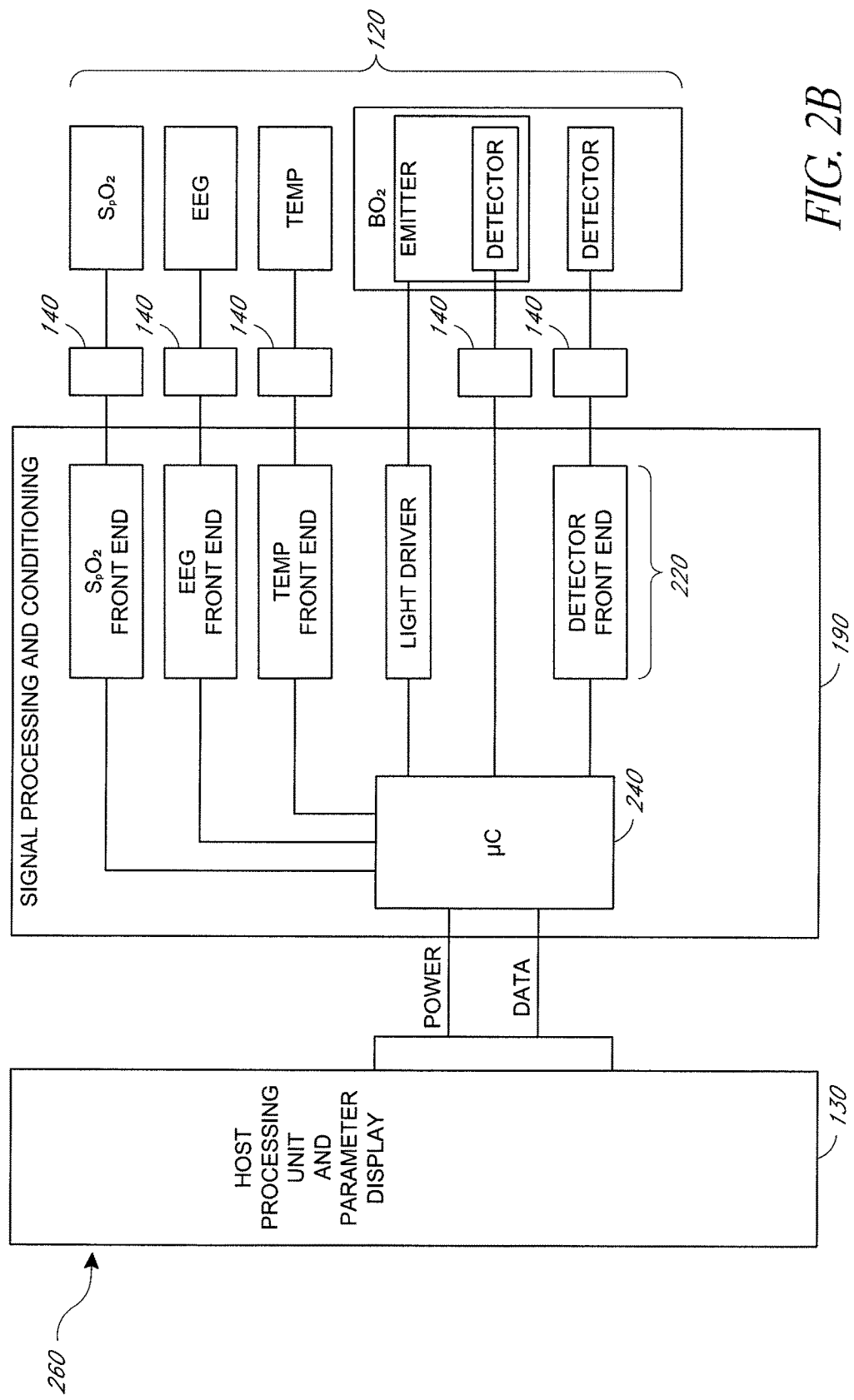
FIGS. 2B-2C illustrate simplified block diagrams of embodiments of a brain oximetry unit, according to the present disclosure.

FIG. 2A illustrates a block diagram of a pulse oximeter system 210. In an embodiment, a signal isolation coupling 140 as shown in FIGS. 3-7) may be integrated into the system between, for example, the detectors 235 and the front-end interface 220, the emitter 230 and the front end interface 220, the front end interface 220 and the signal processor 240, the signal processor 240 and the network interface 250, or any other part of the system that may benefit from a signal isolation coupling 140 (as shown in FIGS. 3-7). FIG. 2B illustrates an embodiment of a block diagram of a patient monitoring system 260 that includes a pulse oximeter 130, a brain oximetry unit (signal processing and conditioning) 190 for processing and conditioning signals from various sensors, and a variety of sensors 120 for detecting various physiological parameters of a patient. Illustrated are $S_pO_2$, EEG, temperature, and brain oximetry sensors 120.

In an embodiment, the sensors 120 may have a front end 220 associated with the sensor 120 included with the brain oximetry unit 190 for controlling the data and power flow between the processor 240 of the brain oximetry unit 190 and the various sensors 120. The front ends 220 communicate drive signals to the various sensors 120 and transmit and/or condition data or signals received from and detected by the sensors 120.

In an embodiment, a signal isolation coupling 140 (as shown in FIGS. 3-7) may be implemented in various places on the patient monitoring system 260. For example, the signal isolation coupling 140 (as shown in FIGS. 3-7) may be implemented between any of the sensors 120 and its corresponding front end 220, any of the front ends 220 and the processor 240 on the brain oximetry unit 190, between the brain oximetry unit 190 and the conventional pulse oximeter 130, or any other suitable location.

Figure 2C:
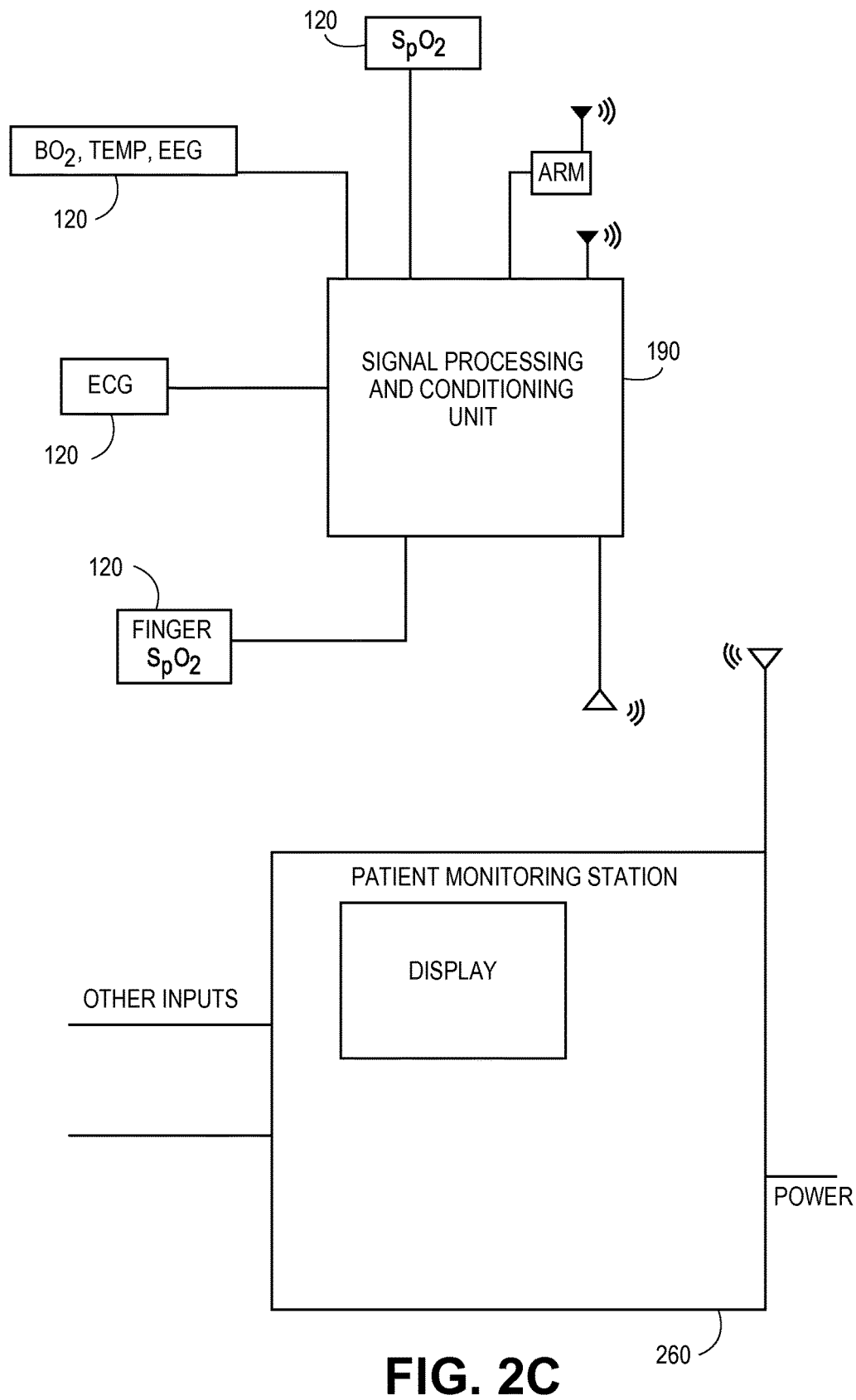

FIG. 2C illustrates an embodiment similar to FIG. 2B including wireless communication with various sensors 120 and between a brain oximetry unit 190 and a monitoring station 260, such as a multiple patient monitoring system or multiple parameter monitoring system.

FIGS. 3-7 illustrate embodiments of signal isolation coupling 140 that may optionally be implemented for various couplings in a medical instrument. In an embodiment, the signal isolation coupling 140 may be achieved through various means including magnetic, optical, radiofrequency links and capacitive coupling. In an embodiment, the magnetic isolation could be a transformer. In another embodiment, an optical coupler could be used for an optical isolation device, in which light from an intensity modulated source passes through an insulating barrier and impinges on a photodetector or other light detector, which recovers the original modulating signal.

In another embodiment, a modulated radio transmitter and demodulation receiver may be implemented to provide a signal isolation coupling 140. In an embodiment where the physical separation is large compared to the wavelength of the radio frequency, electromagnetic wave propagation may be used to provide a coupling connection. In another embodiment, when the transmitter and receiver are located in close proximity, near-field coupling may be used to provide a connection. In an embodiment, near-field coupling may be established magnetically by coils having mutual inductance but insulated from each other, or electrostatically by a small capacitance present across an insulating barrier between the transmitter and receiver circuits. The near field coupling mechanisms may also be used in conjunction with schemes which are not strictly radiofrequency carriers. For example, the ISO721 and related devices, manufactured by Texas Instruments (Dallas, Tex., USA), transmit digital signals across an insulating barrier by means of sensing pulse edges coupled through the tiny capacitance existing across the barrier.

Figure 3A:
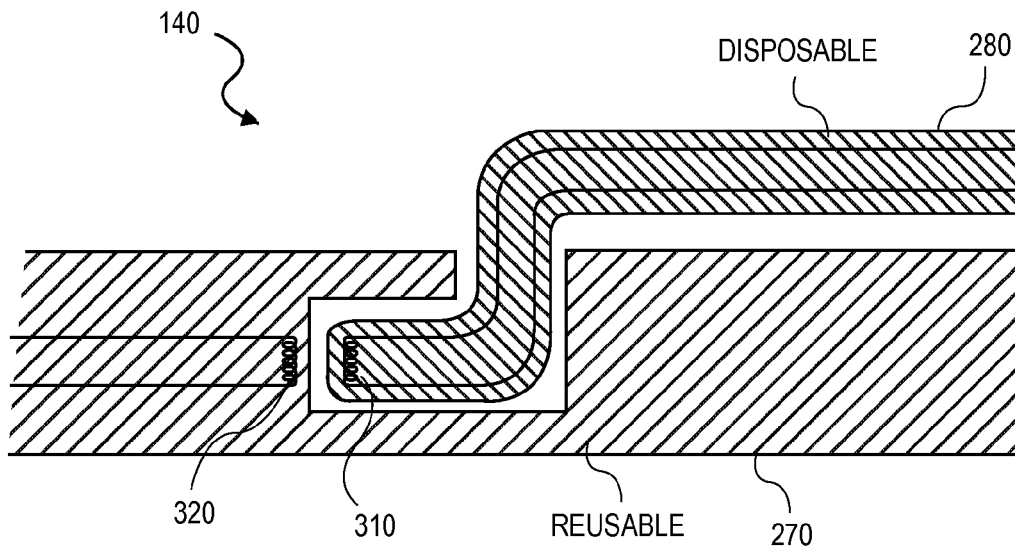
FIGS. 3A-3E illustrate various embodiments of signal isolation coupling, according to the present disclosure. For example.
Figure 3B:
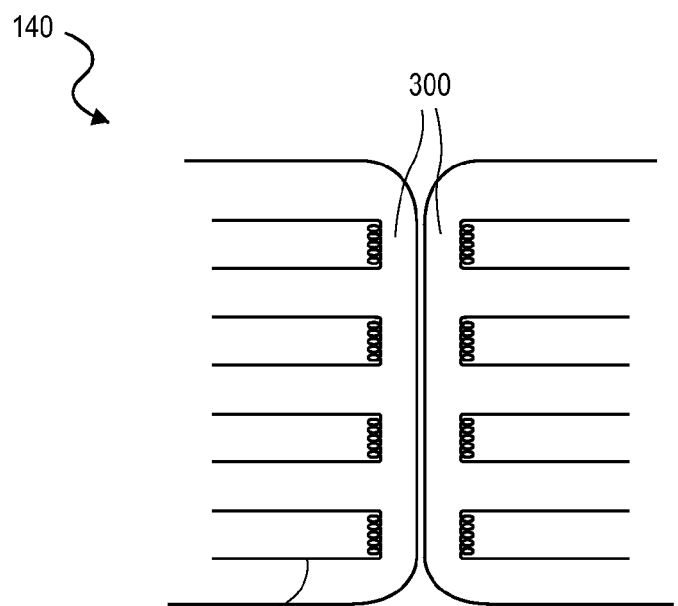

FIG. 3A illustrates an embodiment of a signal isolation coupling 140 connecting the reusable portion 270 and the disposable portion 280 of the combination EEG and cerebral oximetry forehead sensor 120 disclosed herein. The reusable portion 270 and disposable portion 280 of the sensor 210 each have a portion including signal isolation coupling 140 components 290, including transformers to provide an inductance connection. FIG. 3A-3B illustrate an embodiment of the signal isolation coupling 140 with a physical separation between the conductive components.

In an embodiment, an insulating barrier 300 separates the inductive electrical components 290 and provides physical separation between them. In an embodiment, the signal isolation components 290, for example, the transformers, are able to establish an electrical connection across the insulating barrier 300 and physical separation through inductance of the coils. In an embodiment, the insulating barrier 300 provides a connection with fewer or no exposed conductive parts, and insulation of the conductive components by an appropriate electrical insulating material known in the art. In an embodiment, the insulation of the conductive components and reduced exposure of conductive parts allows the connection to be resistant to the ingress of liquids, and may be designed to be free from small cavities that would entrap biological materials.

In an embodiment, the primary winding 310 of the transformer of the signal isolation coupling 140 could be incorporated in the disposable portion 280 of the sensor 120 or other part of a sensor 120 near the patient interface. As illustrated in FIG. 3A the secondary coil 320 could be included in the reusable portion 270 of the sensor 120 or the instrument cable 150 leading to another medical instrument. In this embodiment, the electrical coupling between the patient interface side and instrument side of the signal isolation coupling 140 could be accomplished by bringing the coils into physical proximity, such that they would be magnetically coupled, forming a complete transformer.

In another embodiment, the connection between the reusable portion 270 of the sensor and the cable 150 leading to the instruments, for example the brain oximetry unit 190, conventional pulse oximeter 130 and/or other patient monitoring station 260 may be an optical isolation component.

FIG. 3B illustrates an embodiment of the signal isolation connection 140 with several signal isolation components 290. In one embodiment, the several signal isolation components 290 may be a multitude of transformers placed appropriately to allow the conductors of the primary 310 and secondary coils 320 to be in close proximity with an insulating barrier 300 physically separating the components and preventing direct physical contact between the conductive components of the signal isolation coupling 140.

Although the physical connection is isolated, the two components may be removably held in proximity to one another through a wide variety of attachment mechanisms, including magnetic, straps with catches, Velcro, matable mechanical components, press fit components, adhesives, fasteners of all types, wraps, bandages, or the like. In an embodiment, the proximity mechanism advantageously provides a serilizable environment having a reduced number of cavities or the like that may trap contaminants. In an embodiment, the proximity mechanism is entirely disposable.

Figure 3C:
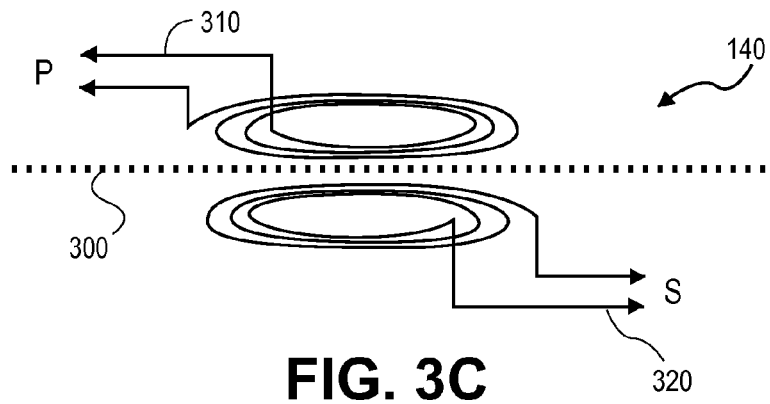
Figure 3D:
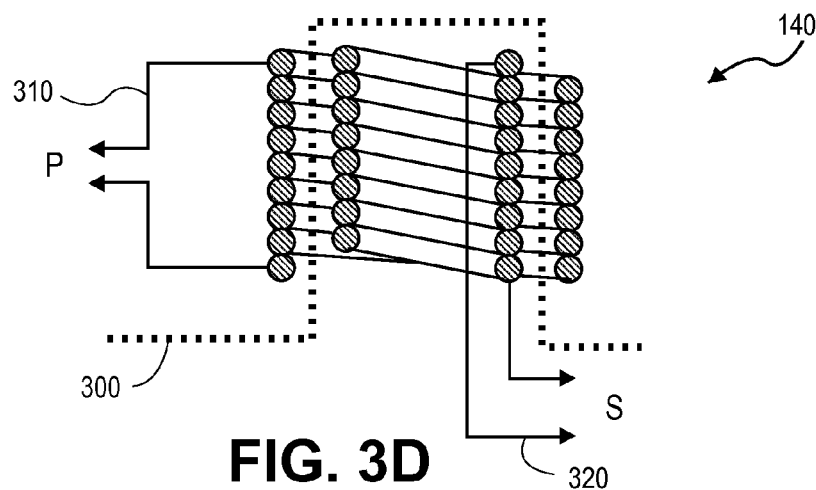

A signal isolation coupling 140 utilizing transformers may take on several embodiments, exemplary embodiments of which are illustrated in FIGS. 3C-3D. For example, the signal isolation coupling 140 may include of a pair of planar coils, where establishing connection of the electrode assembly to the cable includes bringing the coils into proximity face-to-face. An embodiment of this construction is shown in FIG. 3C where the primary coils 310 and secondary planar coils 320 have terminals labeled P and S respectively. The dotted line represents the insulating barrier 300 between the coils, and is also the division along which coils may be separated when the signal isolation coupling 140 is decoupled.

Figure 3E:
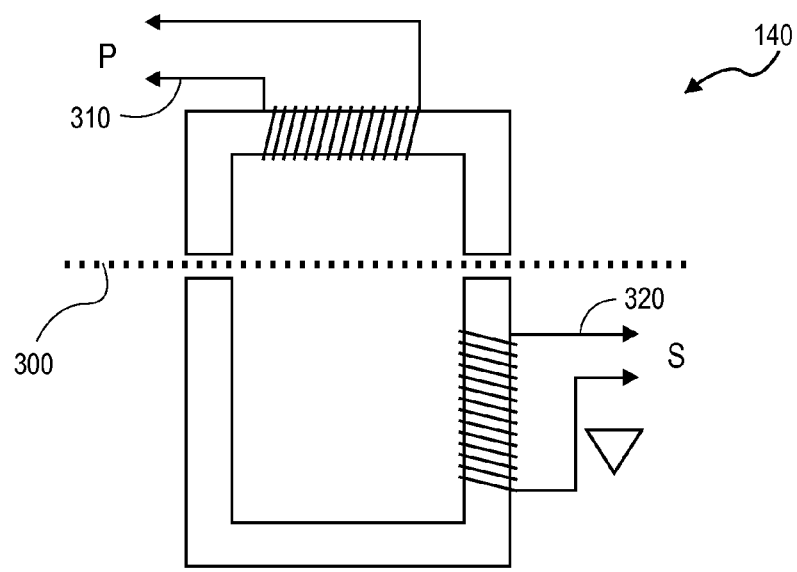

FIG. 3D illustrates an embodiment of a cross-section of a transformer with a pair of co-axial solenoid coils. The heavy dotted line represents the insulating barrier 300 between the coils, and is also the division along which the coils may be separated when the signal isolation coupling 140 is decoupled. In an embodiment, an electrical connection may be established by inserting one coil within the other, and disconnected by drawing the coils apart. In either of these embodiments, a magnetic core may be added to enhance the coupling already present between the coils. FIG. 3E illustrates an embodiment in which the primary coils 310 and secondary coils 320 are not oriented so as to be coupled directly. In this embodiment, a separable magnetic core may be provided to couple the coils when the two parts are brought in proximity of each other.

Bio-potential signals often have low frequencies, often less than about 1 Hz, and tend to be sourced from fairly high impedances. In an embodiment, coupling a signal of this nature may require a transformer having relatively large inductance. A further challenge is that bio-potential signals tend to have relatively small amplitudes, in the millivolt or microvolt range. A transformer configured to pass signals with such characteristics may tend to act as a pickup coil for stray magnetic fields in the vicinity of the subject, such as mains-frequency magnetic fields. In an embodiment, however, various devices may convert the bio-potential signal into a form more suitable for passing through a practical separable transformer or other separable isolation device before passing the signals through the signal isolation coupling 140. In an embodiment, this may be accomplished by adding various electronic circuits to the electrode assembly.

Figure 4A:
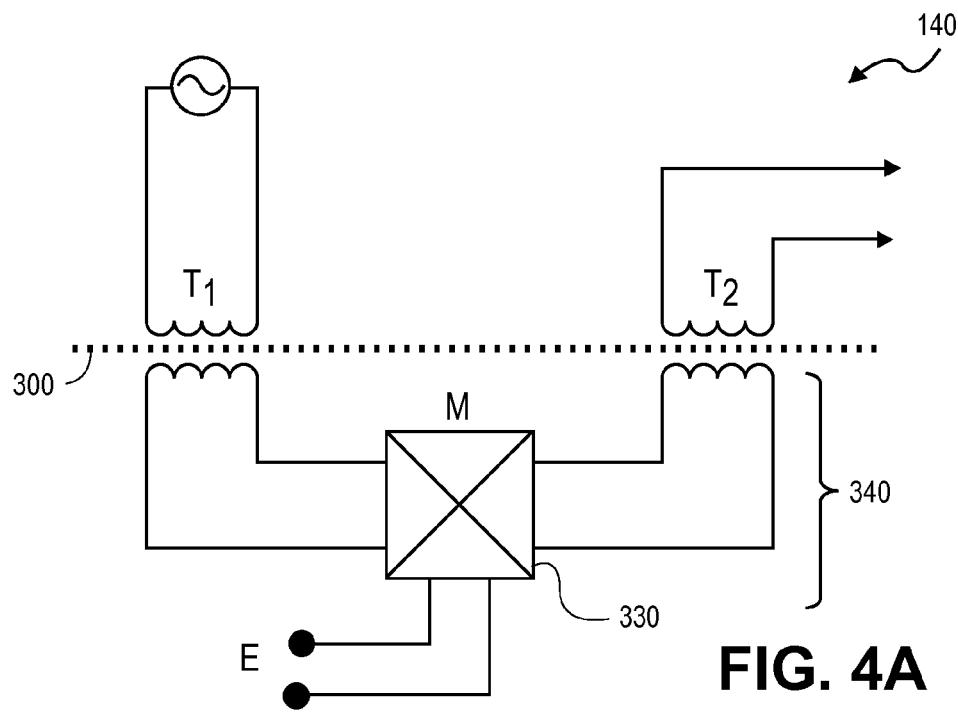
FIGS. 4A-4B illustrate circuit diagrams of a signal isolation connection including a modulator according to an embodiment of the present disclosure.
Figure 4B:
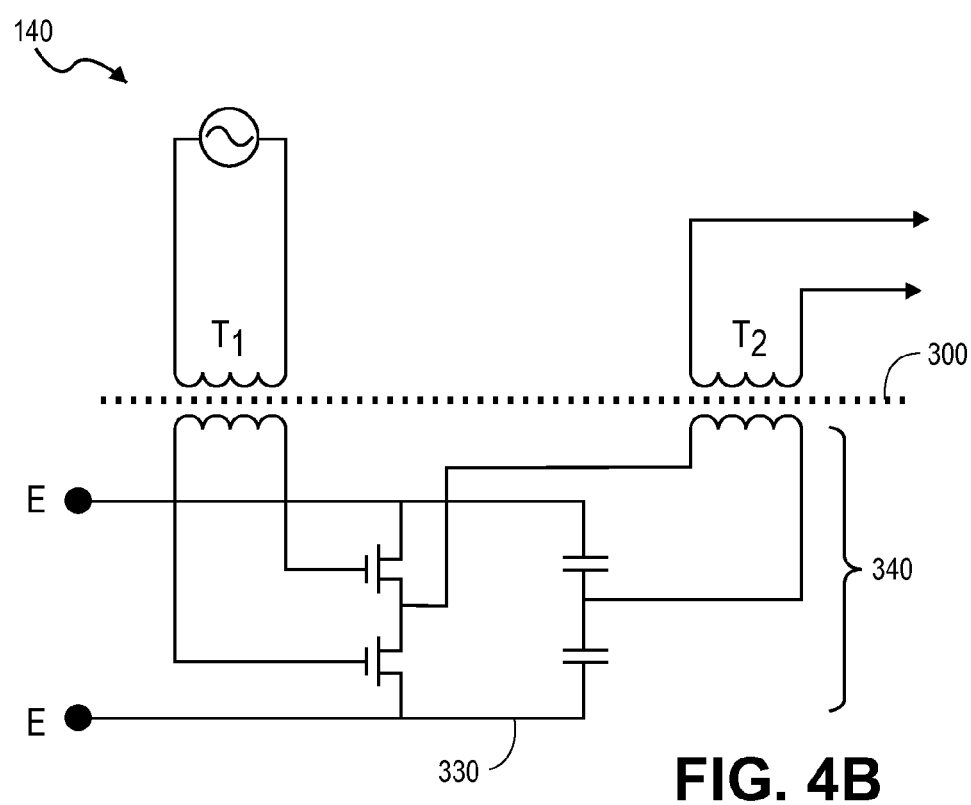

One such embodiment of an electrical system designed to condition a bio-potential signal for passing through a signal isolation coupling 140 utilizing transformers includes a modulator circuit to convert the low-frequency bio-potential signal into a high frequency signal, better suited to be passed through a small and practical separable transformer. In one form of this embodiment, a pair of separable transformers is used, as seen in FIG. 4A. In this embodiment, the electrode assembly 340 including the electrodes E has been equipped with a modulator 330 and one winding each of the transformers T1 and T2. In an embodiment, the transformer T1 passes a carrier frequency excitation from the instrument cable 150 to the electrode assembly. The modulator 330 may then modulate this carrier frequency with the bio-potential signal applied at the electrodes E. The modulated signal is then passed back to the instrument cable through the transformer T2. Both transformers may be of any of the separable forms described herein or other suitable transformers known in the art from the disclosure herein, such that the electrode assembly 340 may be detached from the instrument cable 150 along the dotted line. In embodiments where multiple bio-potential signal channels are involved, a single excitation transformer may be used to serve all channels. The modulator 330 may include of a simple circuit, having no power supply, other than the carrier signal itself. Examples of these suitable modulators 330 would be modulators using diode or transistor switches in any of the many circuit configurations well known in the art from the disclosure herein of constructing modulator and mixer circuits. FIG. 4B illustrates one exemplary modulator 330 circuit topology employing MOSFET switches. This circuit provides simplicity and economy of cost and is readily adaptable to a disposable electrode assembly. However, other embodiments of modulator 330 are possible, and with the application of integrated circuit technology, may be made suitably compact and inexpensive for practical use.

Another embodiment utilizes a single separable transformer to address the difficulties of bio-potential signals. In this embodiment, the electrode assembly 340 includes a parametric modulator circuit connected to the secondary coil of the separable transformer. In an embodiment, the parametric modulator may include of diodes, varactor diodes, or other non-linear devices which change impedance as a function of the bio-potential signals. The bio-potential signal may be observed by measuring the impedance reflected through the separable transformer when an excitation is applied to the transformer's primary coil. In another embodiment, the parametric modulator may generate a harmonic or sub-harmonic of the excitation signal, the amplitude of this harmonic or sub-harmonic being modulated by the bio-potential signal, and being observable at the primary side of the separable transformer.

Figure 5A:
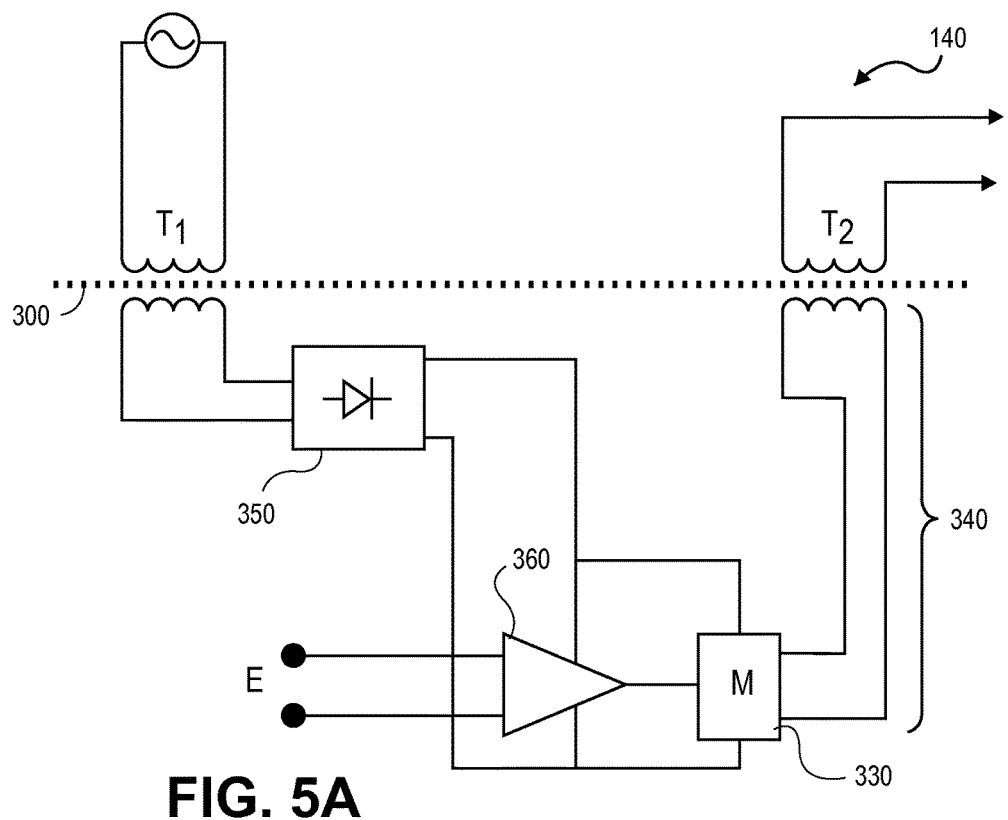
FIGS. 5A-5D illustrate circuit diagrams of a signal isolation connection including amplification of the bio-potential signals according to an embodiment of the present disclosure.

In an embodiment, as discussed herein, the bio-potential signals may be a relatively small amplitude, and it thus may be advantageous to amplify these signals before passing them into the modulator 330 or other similar circuit. Illustrated in FIG. 5A is an embodiment of an amplification circuit designed to be applied to a modulation circuit or directly to a transformer circuit. Shown is the transformer T1 equipped with a rectifier 350, which provides a DC supply voltage to the sensor 120 or other instrumentation device. This voltage supplies an amplifier 360, which amplifies the bio-potential signal acquired by the electrodes E. In an embodiment, the amplified signal is then applied to the modulator 330, which returns a modulated signal to the instrument cable 150 by means of the transformer T2.

However, as a power supply voltage is now available to the modulator 330, it may have an expanded scope of operation as compared to the embodiment illustrated in FIGS. 4A-4B. For example, it may modulate the carrier frequency supplied through T1, as before. However, it may develop its own, different carrier frequency, and may use any manner of various modulation schemes, such as amplitude, phase, or frequency modulation. In an embodiment, it may include an analog to digital converter, digital signal processing, and other functions and circuits, such that its output is a digital representation of the original bio-potential signal. This digital representation may be coupled directly through the transformer T2 or may be modulated, by any of the various means known in the art, on a carrier signal before being passed through the transformer T2.

Figure 5B:
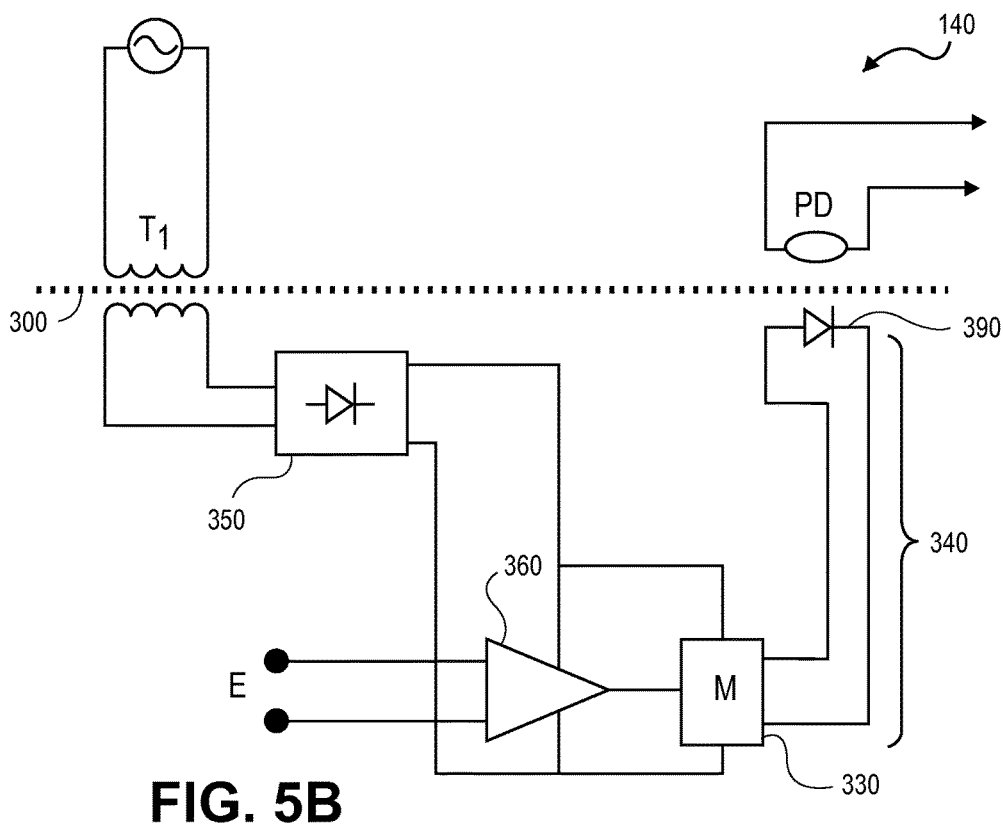

In other embodiments of the signal isolation coupling 140, the transformer T2 may be replaced with other types of devices. For example, the receiving coil of the transformer T2 may be replaced with some other suitable magnetic sensor, such as a GMR device. In another embodiment, the receiving coil of the transformer T2 may be replaced with some coupling device(s) not operating on a magnetic principle. For example, FIG. 5B illustrates the use of an optical coupling scheme, where the modulator 330 drives an LED or other optical light source 390, the radiation from which impinges on the photodetector PD which is integrated into the instrument cable 150. The dotted line indicates the insulating barrier 300 and the physical separation of the signal isolation coupling 140. In an embodiment, the material of the insulating barrier 300 may be substantially transmissive of the radiation of the light source 390.

Figure 5C:
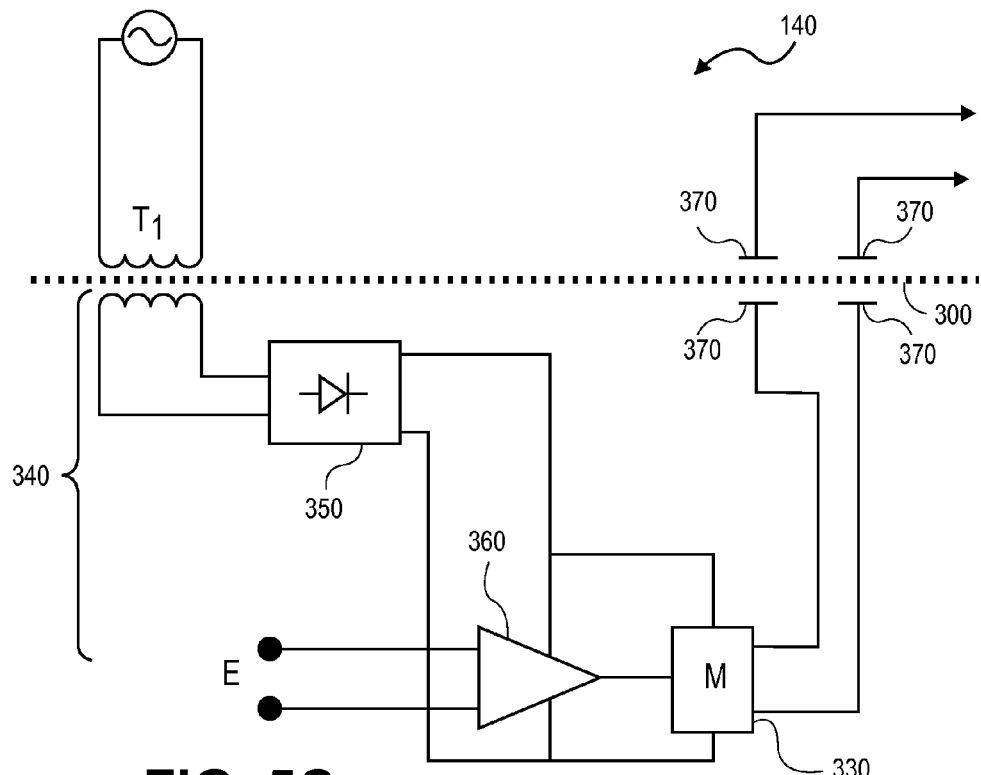
Figure 5D:
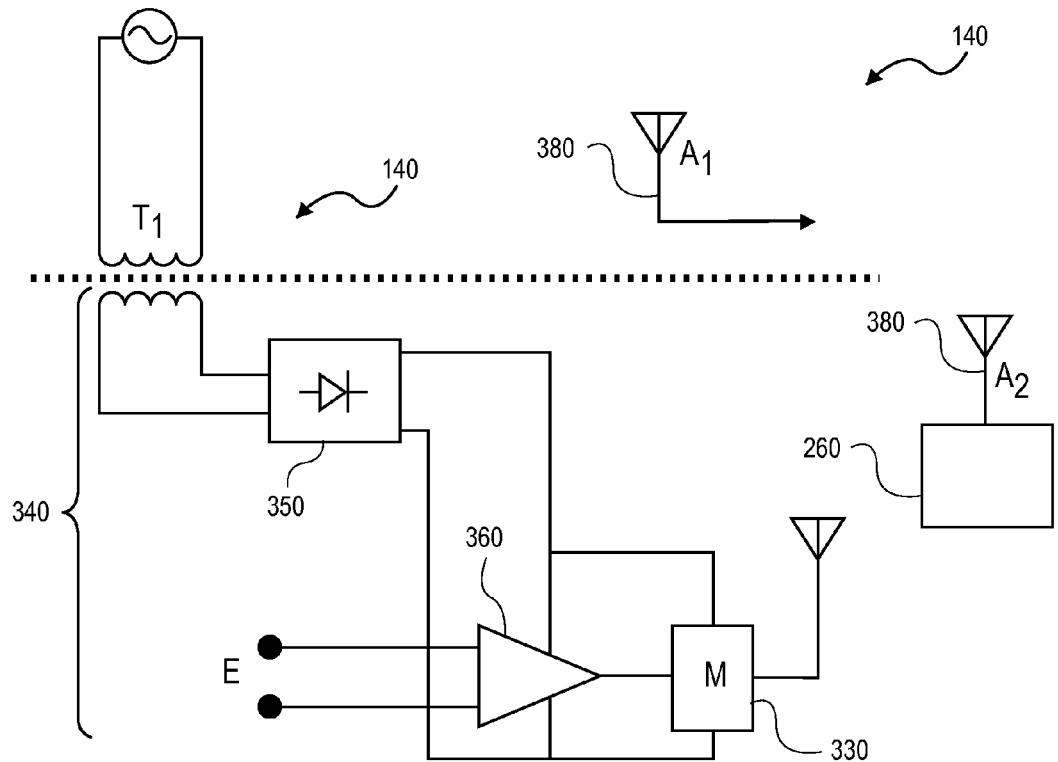

In the case of an optical link, the modulator 330 may not be necessary, since the optical link can be designed to have adequate low frequency response, such that the baseband bio-potential signal can be directly passed. In another embodiment, as illustrated in FIG. 5C, an electrostatic coupling is created using the capacitance between small coupling conductors 370 placed on opposite sides of the insulating barrier 300. In another embodiment, the modulator 330 includes an antenna 380 to transmit its output and/or receive input instructions, as seen in FIG. 5D. The radiated signal may be received either by an antenna A1 located in close proximity in the instrument cable connector 140, or by an antenna A2 located remotely, such as within a remote patient monitoring station 260. In this latter case, in an embodiment, the instrument cable 150 may be used to supply power to the electronics within the electrode assembly 340, while the return of the bio-potential is transmitted wirelessly.

In the embodiment shown in FIGS. 5A-5D it is possible to operate the system without the transformer T1 and the rectifier 350. In an embodiment, the disposable portion 280 of the sensor 120 may operate only for a short period of time, such as for the duration of a particular medical procedure. In another embodiment, where long term monitoring of the bio-potential signal may be desired, the electrodes may have a finite lifetime, for example, due to drying out and similar chemical effects. Therefore, the power supplied by the transformer T1 and the rectifier 350 may instead be obtained from a small battery imbedded, for example, in the disposable portion 280 of the sensor 120. By the use of suitable low power electronic design techniques, balanced with appropriate selection of the battery type, sufficient battery life for many limited-time applications of the disposable portion 280 of the sensor 120 can be obtained. The coupling modalities illustrated in the various parts of FIGS. 5A-5D may also be adapted to battery operation. However, some have lower power requirements than others, and therefore may be better suited to particular intended service durations.

In the embodiments illustrated in the various parts of FIGS. 5A-5D, with either transformer or battery power, multiple channels of bio-potential signals obtained from additional electrodes may be multiplexed through a single coupling device of any of the types illustrated.

Figure 6:
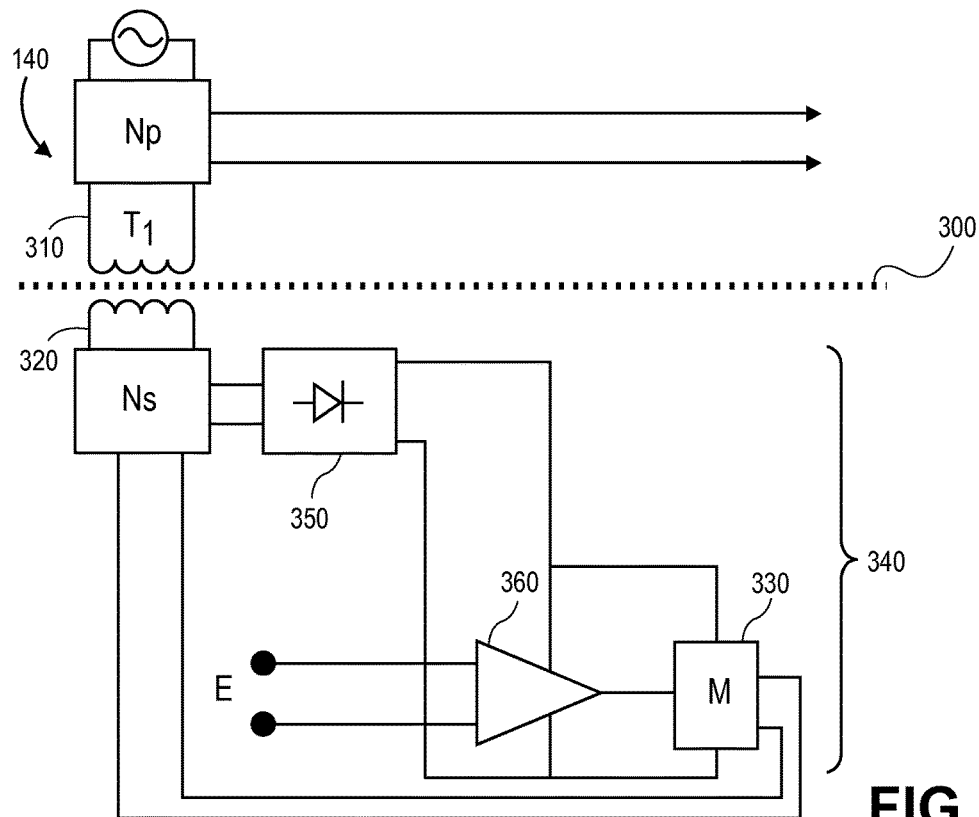
FIGS. 6-7 illustrate circuit diagrams of a signal isolation connection employing alternate power sources according to an embodiment of the present disclosure.

As illustrated in FIG. 6, it is possible to avoid the use of a battery while using a single coupling device for the signal isolation coupling 140. In an embodiment, the transformer T1 may serve as the coupling device. In this embodiment, the primary coil 310 and secondary coil 320 of the transformer T1 may be equipped with 3-port networks Np and Ns respectively. These are duplexing networks, which allow the power and modulated data to pass independently in opposite directions through the transformer T1. For example, in an embodiment, where the modulator 330 uses a carrier frequency higher than the power frequency, the networks would take the form of filters having high pass and low pass ports. In that embodiment, the networks Ns would extract the power through the low-pass port and apply it the rectifier 350. The modulator 330 would feed its output back through the high-pass port. Also, the network Np would apply power through its low-pass port and extract the modulator 330 signal through the high-pass port. Note that the modulated signal may be either an analog or digital representation of the bio-potential signal. Further, note that multiple bio-potential channels, from additional electrodes, may be multiplexed in either analog or digital format through the single transformer.

Figure 7:
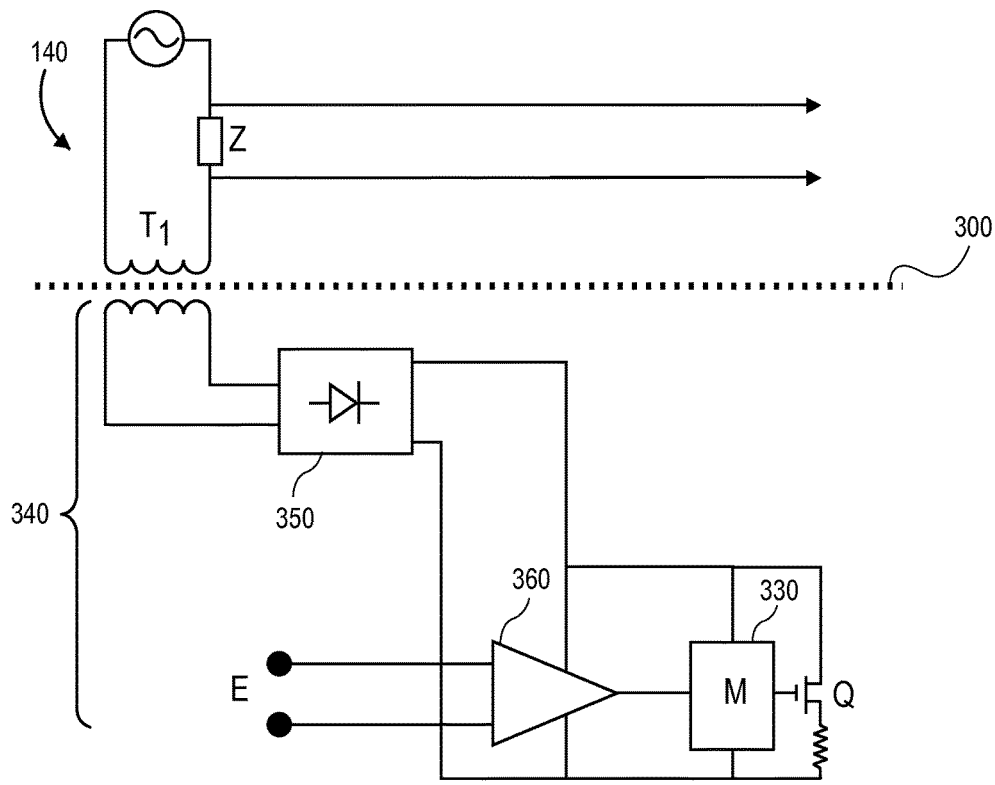

FIG. 7 illustrates another embodiment of a signal isolation coupling 140 which duplexes both power and signal through a single transformer. Shown is the output of the modulator 330 being used to operate a load device. In an embodiment, the load device then presents a variable load to the DC power developed by the rectifier 350, in response to the modulated output. In FIG. 7, this is represented as transistor Q. The modulator 330 output is therefore reflected on the power supply current passed through the transformer T1, and may be recovered by monitoring this current. For example, an impedance Z placed in the power excitation circuit will develop a voltage representative of the modulator signal. Note that this is possible to eliminate the modulator 330, and apply the amplified baseband bio-potential signal to Q. In this embodiment, the supply current becomes modulated with the baseband signal, and impedance Z recovers an AM modulated voltage representative of the original biopotential signal. In an alternate embodiment, the load device maybe designed to be operated with an AC voltage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

In an embodiment, a device designer can use a system for isolation of electrical components of a physiological monitoring system that comprises a sensor for detecting an indication of a physiological parameter, a patient monitoring system for displaying information transmitted from the sensor, an instrument cable connecting the sensor and the patient monitoring system, a sensor cable connecting the sensory components of the sensor to the instrument cable and a signal isolation coupling located along the sensor cable. This system could utilize an EEG sensor, a pulse oximeter, or a combination cerebral oximeter and EEG forehead sensor. The EEG forehead sensor may include a disposable portion that contains an EEG electrode cable connecting a set of EEG electrodes to the sensor cable. The EEG electrode cable may include a signal isolation coupling which may include an insulating barrier, or inductive components, for example, transformers. In some embodiments, the cerebral oximeter may be reusable.

A device designer may use a forehead sensor for isolation of electrical components of the sensor that includes at least one sensory component for detecting an indication of a physiological parameter of a patient, a sensor cable connected to the at least one sensory component for providing power and communication to the at least one sensory component, and a signal isolation coupling along the sensor cable. The at least one sensory component may be a plurality of EEG electrodes, a cerebral oximeter or pulse oximeter.

In an embodiment, a device designer can use a combination cerebral oximeter and EEG forehead sensor for isolation of electrical components that includes a reusable portion containing cerebral oximetry sensory components capable of detecting the cerebral oxygenation of matter inside the cerebral cavity, a disposable portion containing EEG electrodes capable of detecting electrical activity on a patient's skin, a disposable cable connecting the EEG electrodes to the reusable portion, and a signal isolation coupling connecting the disposable cable to the reusable portion. The sensor's signal isolation coupling may completely surround the signal isolation coupling to allow easy cleaning of the signal isolation coupling.

Additionally, all publications, patents, and patent applications mentioned in this specification are herein incorporated by reference to the same extent as if each individual publication, patent, or patent application was specifically and individually indicated to be incorporated by reference.

What is claimed is:

1. A system for connecting a sensor using isolation of electrical components comprising:
   a noninvasive optical sensor including a light source configured to emit light and a detector configured to detect the light after attenuation by body tissue at a measurement site;
   an EEG sensor comprising a plurality of EEG electrodes configured to detect a bioelectric signal from a patient;
   a first cable including a first plurality of conductors electrically connected to the EEG sensor and the noninvasive optical sensor;
   a second cable including a second plurality of conductors coupled to a patient monitoring system; and
   a signal isolation coupling comprising:
      a first electrical element inside the first cable and forming a part of the first cable, said first electrical element electrically connected to said first plurality of conductors via a modulator circuit inside the first cable, wherein said modulator circuit is configured to transform low frequency signals carried by the first plurality of conductors to high frequency signals;
      a first insulating barrier inside the first cable protecting the first portion;
      a second electrical element inside the second cable and forming a part of the second cable, said second electrical element electrically connected to the second plurality of conductors, said second plurality of conductors configured to carry said high frequency signals received by the second electrical element from the first electrical element over a physical separation between the first cable and the second cable, wherein said second cable is configured to detachably connect with the first cable at the physical separation; and
      a second insulating barrier inside the second cable protecting the second portion;
   wherein the first cable comprises a cavity configured to receive the second cable and electrically couple with the second cable at the physical separation with no exposed conductors, the cavity comprising a first section and a second section, the first section perpendicular to the second section, and wherein the cavity is configured to secure the first cable with the second cable through the first and the second sections.

2. The system of claim 1 further comprising an attachment mechanism configured to removably hold the first cable proximate the second cable and configured to orient the first electrical element to couple with the second electrical element.

3. The system of claim 2, wherein the attachment mechanism comprises matable mechanical components.

4. The system of claim 1, wherein the first electrical element comprises a first coil and wherein the second electrical element comprises a second coil responsive to the first coil.

5. A system for connecting a sensor using isolation of electrical components comprising:
   a first cable comprising:
      one or more first conductors electrically coupled to a sensor configured to detect low voltage signals;
      a first electrical element coupled to the one or more first conductors and transfer the detected low voltage signal across a gap; and
      a first insulating barrier configured to insulate the first electrical element; a second cable comprising:
      one or more second conductors electrically coupled to a patient monitor;
      a second electrical element coupled to the one or more second conductors and configured to receive the transferred detected low voltage signals across the gap; and
      a second insulating barrier configured to insulate the second electrical element; and
   the first cable comprises an attachment mechanism configured to removable secure the first cable with the second cable, the attachment mechanism comprises a cavity comprising a first section and a second section, the first section perpendicular to the second section, wherein the cavity is configured to secure the first cable with the second cable through the first and the second sections;
wherein the one or more first conductors and the first electrical element are isolated from the one or more second conductors and the second electrical element.

\* \* \* \* \*